US011896420B2

(12) United States Patent
Martin et al.

(10) Patent No.: US 11,896,420 B2
(45) Date of Patent: Feb. 13, 2024

(54) AUSCULTATORY SOUND-OR-VIBRATION SENSOR

(71) Applicant: AUSCULSCIENCES, INC., Vienna, VA (US)

(72) Inventors: Simon Martin, Gatineau (CA); Mark W. Armstrong, Ottawa (CA); Anthony Dewar, Ottawa (CA); Robert J. Griffin, Kanata (CA); Brady Laska, Arnprior (CA); Sergey A. Telenkov, Ottawa (CA); Steven P. Morton, Kanata (CA); Camilla Jastrzebski, Ottawa (CA)

(73) Assignee: AUSCULSCIENCES, INC., Vienna, VA (US)

( * ) Notice: Subject to any disclaimer, the term of this patent is extended or adjusted under 35 U.S.C. 154(b) by 0 days.

(21) Appl. No.: 17/994,319

(22) Filed: Nov. 27, 2022

(65) Prior Publication Data

US 2023/0091977 A1 Mar. 23, 2023

Related U.S. Application Data

(62) Division of application No. 17/179,884, filed on Feb. 19, 2021, now Pat. No. 11,510,644, which is a
(Continued)

(51) Int. Cl.
*A61B 7/02* (2006.01)
*A61B 7/04* (2006.01)
(Continued)

(52) U.S. Cl.
CPC ............ *A61B 7/026* (2013.01); *A61B 5/6805* (2013.01); *A61B 7/003* (2013.01); *A61B 7/04* (2013.01);
(Continued)

(58) Field of Classification Search
CPC ....... A61B 7/026; A61B 5/6805; A61B 7/003; A61B 7/04; A61B 2562/0204;
(Continued)

(56) References Cited

U.S. PATENT DOCUMENTS

| 1,657,078 A | 1/1928 | Frederick et al. |
| 1,658,327 A | 2/1928 | Dodge |

(Continued)

FOREIGN PATENT DOCUMENTS

| AU | 2004200275 B2 | 2/2004 |
| CA | 3025748 A1 | 12/2017 |

(Continued)

OTHER PUBLICATIONS

US 8,740,816 B2, 06/2014, Telfort et al. (withdrawn)
(Continued)

*Primary Examiner* — Andrew L Sniezek
(74) *Attorney, Agent, or Firm* — Kurt L. VanVoorhies

(57) ABSTRACT

A metallic diaphragm disk incorporating a piezoelectric material bonded thereto and operatively coupled to a base rim of a housing provides for closing an open-ended cavity at the first end of the housing. At least one inertial mass is either incorporated in or attached to the housing. A plastic film adhesively bonded to at least one of an outer rim of the housing or an outer-facing surface of the disk provides for receiving an adhesive acoustic interface material to provide for coupling the housing to the skin of a test subject.

14 Claims, 22 Drawing Sheets

Related U.S. Application Data division of application No. 16/152,004, filed on Oct. 4, 2018, now Pat. No. 10,925,573.

(60) Provisional application No. 62/568,155, filed on Oct. 4, 2017.

(51) Int. Cl.
  *A61B 7/00* (2006.01)
  *A61B 5/00* (2006.01)
  *B06B 1/08* (2006.01)
  *G01H 11/08* (2006.01)
  *B06B 1/06* (2006.01)
  *H04R 17/02* (2006.01)

(52) U.S. Cl.
  CPC ............ *B06B 1/0688* (2013.01); *B06B 1/085* (2013.01); *G01H 11/08* (2013.01); *H04R 17/02* (2013.01); *A61B 2562/0204* (2013.01); *A61B 2562/221* (2013.01); *A61B 2562/225* (2013.01); *B06B 2201/76* (2013.01)

(58) Field of Classification Search
  CPC ........ A61B 2562/221; A61B 2562/225; B06B 1/0688; B06B 1/085; B06B 2201/76; G01H 11/08
  See application file for complete search history.

(56) References Cited

U.S. PATENT DOCUMENTS

| | | | |
|---|---|---|---|
| 3,130,275 | A | 4/1964 | Hagey |
| 3,283,181 | A | 11/1966 | Johanson |
| 3,573,394 | A | 4/1971 | Birnbaum |
| 3,682,161 | A | 8/1972 | Alibert |
| 3,868,954 | A | 3/1975 | Jeda |
| 4,012,604 | A | 3/1977 | Speidel |
| 4,295,471 | A | 10/1981 | Kaspari |
| 4,308,870 | A | 1/1982 | Arkans |
| 4,556,066 | A | 12/1985 | Semrow |
| 4,592,366 | A | 6/1986 | Sainomoto et al. |
| 4,672,976 | A | 6/1987 | Kroll |
| 4,672,977 | A | 6/1987 | Kroll |
| 4,805,633 | A | 2/1989 | Kotani |
| 4,947,859 | A | 8/1990 | Brewer |
| 4,967,760 | A | 11/1990 | Bennett, Jr. et al. |
| 4,989,611 | A | 2/1991 | Zanetti et al. |
| 4,995,473 | A * | 2/1991 | Packard ............... A61B 7/02 181/131 |
| 5,002,060 | A | 3/1991 | Nedivi |
| 5,003,605 | A | 3/1991 | Phillipps |
| 5,035,247 | A | 7/1991 | Heimann |
| 5,036,857 | A | 8/1991 | Semmlow et al. |
| 5,086,776 | A | 2/1992 | Fowler, Jr. |
| 5,109,863 | A | 5/1992 | Semmlow et al. |
| 5,159,932 | A | 11/1992 | Zanetti |
| 5,309,922 | A | 5/1994 | Schechter |
| RE34,663 | E | 7/1994 | Seale |
| 5,365,937 | A | 11/1994 | Reeves |
| 5,467,775 | A | 11/1995 | Callahan |
| 5,494,043 | A | 2/1996 | O'Sullivan |
| 5,566,671 | A | 10/1996 | Lyons |
| 5,595,188 | A | 1/1997 | Kassal |
| 5,602,924 | A | 2/1997 | Durand |
| 5,807,268 | A | 9/1998 | Reeves |
| 5,827,198 | A | 10/1998 | Kassal |
| 5,885,222 | A | 3/1999 | Kassal |
| 5,913,829 | A | 6/1999 | Reeves |
| 6,050,950 | A | 4/2000 | Mohler |
| 6,053,872 | A | 4/2000 | Mohler |
| 6,152,879 | A | 11/2000 | Mohler |
| 6,179,783 | B1 | 1/2001 | Mohler |
| 6,261,237 | B1 | 7/2001 | Swanson et al. |
| 6,278,890 | B1 | 8/2001 | Chassaing et al. |
| 6,478,744 | B2 | 11/2002 | Mohler |
| 6,491,647 | B1 | 12/2002 | Bridger et al. |
| 6,544,189 | B2 | 4/2003 | Watrous |
| 6,661,161 | B1 | 12/2003 | Lanzo et al. |
| 6,699,204 | B1 | 3/2004 | Kehyayan et al. |
| 6,780,159 | B2 | 8/2004 | Sandler et al. |
| 6,790,183 | B2 | 9/2004 | Murphy |
| 6,878,117 | B1 | 4/2005 | Watrous |
| 7,010,342 | B2 | 3/2006 | Galen et al. |
| 7,037,268 | B1 | 5/2006 | Sleva et al. |
| 7,082,202 | B1 | 7/2006 | Orten |
| 7,110,804 | B2 | 9/2006 | Baumer et al. |
| 7,248,923 | B2 | 7/2007 | Maile et al. |
| 7,302,290 | B2 | 11/2007 | Bauer |
| 7,351,207 | B2 | 4/2008 | Priemer |
| 7,416,531 | B2 | 8/2008 | Mohler |
| 7,517,319 | B2 | 4/2009 | Kushnir et al. |
| 7,527,597 | B2 | 5/2009 | Sandler et al. |
| 7,668,589 | B2 | 2/2010 | Bauer |
| 7,670,298 | B2 | 3/2010 | Carlson et al. |
| 7,726,209 | B2 | 6/2010 | Ruotoistenmaki |
| 7,828,740 | B2 | 11/2010 | Longhini et al. |
| 7,844,334 | B2 | 11/2010 | Maile et al. |
| 7,909,772 | B2 | 3/2011 | Popev et al. |
| 7,998,091 | B2 | 8/2011 | Carim et al. |
| 8,007,442 | B2 | 8/2011 | Carlson et al. |
| 8,024,974 | B2 | 9/2011 | Bharti et al. |
| 8,064,610 | B2 | 11/2011 | Ward et al. |
| 8,277,389 | B2 | 10/2012 | Carlson et al. |
| 8,333,718 | B2 | 12/2012 | Carim et al. |
| 8,535,235 | B2 | 9/2013 | Carlson et al. |
| 8,657,742 | B2 | 2/2014 | Neumann |
| 8,690,799 | B2 | 4/2014 | Telfort et al. |
| 8,702,627 | B2 | 4/2014 | Telfort et al. |
| 8,715,206 | B2 | 5/2014 | Telfort et al. |
| 8,755,535 | B2 | 6/2014 | Telfort et al. |
| 8,755,872 | B1 | 6/2014 | Marinow |
| 8,771,204 | B2 | 7/2014 | Telfort et al. |
| 8,801,613 | B2 | 8/2014 | Al-Ali et al. |
| 8,821,415 | B2 | 9/2014 | Al-Ali et al. |
| 8,827,919 | B2 | 9/2014 | Siejko et al. |
| 8,845,544 | B2 | 9/2014 | Carlson et al. |
| 8,870,792 | B2 | 10/2014 | Al-Ali et al. |
| 8,972,002 | B2 | 3/2015 | Wariar et al. |
| 9,017,269 | B2 | 4/2015 | Endo et al. |
| 9,101,274 | B2 | 8/2015 | Bakema et al. |
| 9,125,574 | B2 | 9/2015 | Zia et al. |
| 9,226,726 | B1 | 1/2016 | Semmlow |
| 9,320,489 | B1 | 6/2016 | Semmlow |
| 9,386,961 | B2 | 7/2016 | Al-Ali et al. |
| 9,436,645 | B2 | 9/2016 | Al-Ali et al. |
| 9,521,956 | B2 | 12/2016 | Bedingham et al. |
| 9,795,358 | B2 | 10/2017 | Telfort et al. |
| 9,955,939 | B2 | 5/2018 | Sezan et al. |
| 10,441,181 | B1 | 10/2019 | Telfort et al. |
| 10,555,717 | B2 | 2/2020 | Hsu et al. |
| 10,925,573 | B2 | 2/2021 | Martin et al. |
| 11,045,144 | B2 | 6/2021 | Zhou et al. |
| 11,045,163 | B2 | 6/2021 | Laska et al. |
| 11,191,486 | B2 | 12/2021 | Griffin et al. |
| 11,284,827 | B2 | 3/2022 | Telenkov et al. |
| 2001/0030077 | A1* | 10/2001 | Watson ................. A61B 5/742 381/67 |
| 2003/0176801 | A1 | 9/2003 | Galen et al. |
| 2004/0032957 | A1 | 2/2004 | Mansy et al. |
| 2005/0033144 | A1 | 2/2005 | Wada |
| 2005/0124902 | A1 | 6/2005 | Baumer et al. |
| 2005/0232434 | A1 | 10/2005 | Andersen |
| 2005/0245834 | A1 | 11/2005 | Baumer et al. |
| 2005/0273015 | A1 | 12/2005 | Baumer et al. |
| 2007/0113654 | A1 | 5/2007 | Carim et al. |
| 2007/0165872 | A1* | 7/2007 | Bridger .................... A61B 7/04 600/528 |
| 2008/0021336 | A1 | 1/2008 | Dubak, III |
| 2008/0093157 | A1 | 4/2008 | Drummond et al. |
| 2009/0216138 | A1 | 8/2009 | Arand et al. |
| 2010/0087746 | A1 | 4/2010 | Radzievsky et al. |
| 2010/0094152 | A1 | 4/2010 | Semmlow |
| 2011/0066041 | A1 | 3/2011 | Pandia et al. |

(56) References Cited

U.S. PATENT DOCUMENTS

| | | |
|---|---|---|
| 2011/0066042 A1 | 3/2011 | Pandia et al. |
| 2011/0077707 A1 | 3/2011 | Maile et al. |
| 2011/0098583 A1 | 4/2011 | Pandia et al. |
| 2011/0125060 A1 | 5/2011 | Telfort et al. |
| 2011/0137210 A1 | 6/2011 | Johnson |
| 2011/0263994 A1 | 10/2011 | Burns et al. |
| 2012/0209132 A1 | 8/2012 | Jones et al. |
| 2013/0109989 A1 | 5/2013 | Busse et al. |
| 2013/0131465 A1 | 5/2013 | Yamamoto et al. |
| 2013/0231576 A1 | 9/2013 | Tanaka et al. |
| 2013/0252219 A1 | 9/2013 | Lecat |
| 2014/0046138 A1 | 2/2014 | Merk et al. |
| 2014/0221772 A1 | 8/2014 | Wolloch et al. |
| 2014/0243616 A1 | 8/2014 | Johnson |
| 2015/0038856 A1 | 2/2015 | Houlton et al. |
| 2015/0320323 A1 | 11/2015 | Bakema et al. |
| 2015/0327810 A1 | 11/2015 | Horii et al. |
| 2016/0310108 A1 | 10/2016 | Flynn |
| 2017/0079594 A1 | 3/2017 | Telfort et al. |
| 2017/0086778 A1 | 3/2017 | Cahan et al. |
| 2017/0188868 A1 | 7/2017 | Kale et al. |
| 2018/0132815 A1 | 5/2018 | Tsai et al. |
| 2018/0242926 A1 | 8/2018 | Muhsin et al. |
| 2018/0247712 A1 | 8/2018 | Muhsin et al. |
| 2018/0300919 A1 | 10/2018 | Muhsin et al. |
| 2019/0059748 A1 | 2/2019 | Kaiser et al. |
| 2019/0083038 A1 | 3/2019 | Griffin et al. |
| 2019/0175072 A1 | 6/2019 | Schmidt et al. |
| 2019/0298269 A1 | 10/2019 | Atashbar et al. |
| 2019/0365263 A1 | 12/2019 | Raj et al. |
| 2020/0060629 A1 | 2/2020 | Muhsin et al. |
| 2020/0121205 A1 | 4/2020 | Telfort et al. |
| 2020/0178924 A1 | 6/2020 | Hsu et al. |

FOREIGN PATENT DOCUMENTS

| | | | |
|---|---|---|---|
| CN | 201727511 U | 2/2011 | |
| DE | 10046703 B4 | 3/2005 | |
| EP | 194823 A2 | 9/1986 | |
| EP | 325805 A2 | 8/1989 | |
| EP | 2710959 A1 | 3/2014 | |
| EP | 2765909 B1 | 6/2019 | |
| JP | 2008302052 A | 12/2008 | |
| JP | 2012200382 A1 | 10/2012 | |
| WO | 9008506 A1 | 8/1990 | |
| WO | 9826716 A1 | 6/1998 | |
| WO | 9923940 A1 | 5/1999 | |
| WO | 0122884 A1 | 4/2001 | |
| WO | 03077731 A2 | 9/2003 | |
| WO | 2005055287 A2 | 6/2005 | |
| WO | 2006020764 A2 | 2/2006 | |
| WO | 2006067217 A2 | 6/2006 | |
| WO | WO-2006073854 A1 * | 7/2006 | ............... A61B 7/02 |
| WO | 2008036911 A2 | 3/2008 | |
| WO | 2011047213 A1 | 4/2011 | |
| WO | 2017037678 A1 | 3/2017 | |
| WO | 2017216374 A1 | 12/2017 | |
| WO | 2019060455 A1 | 3/2019 | |

OTHER PUBLICATIONS

Vermarien et al., "The Recording of Heart Vibrations: A Problem of Vibration Measurement on Soft Tissue", Med. & Biol. Eng. & Comput. 1984, 22, pp. 168-178.

Timanin et al., "Mechanical Impedance of Biological Soft Tissues: Possible Models," Russian Journal of Biomechanics, vol. 3, No. 4, 1999.

European Patent Office International Search Report and Written Opinion of International Searching Authority in International Application No. PCT/US2018/054471, dated May 6, 2019, 18 pp.

Schmidt, Samuel, Detection of Coronary Artery Disease with an Electric Stethoscope, PHD Thesis, Aalborg University, Aalborg, Denmark, 2011, 49 pp.

Novise Medical Inc, "Audicor 200S", 2009, 2 pp. brochure downloaded from www.audiocore.com on Sep. 14, 2020.

* cited by examiner

FIG. 7a
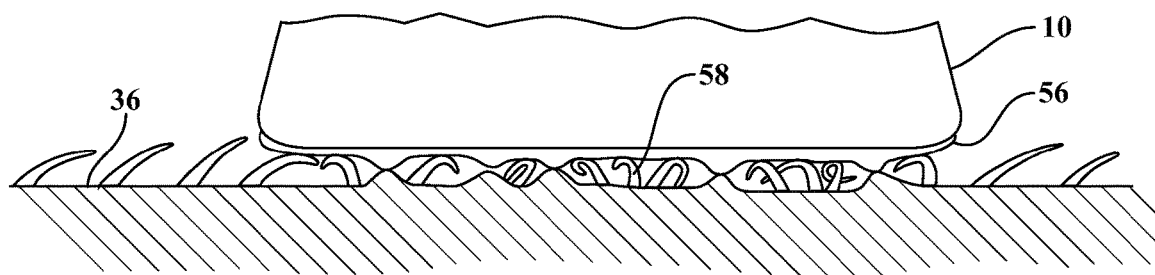
FIG. 7b
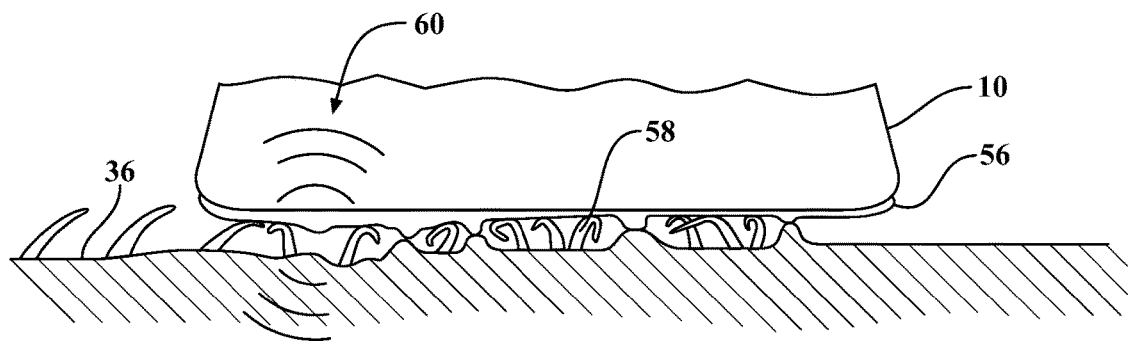
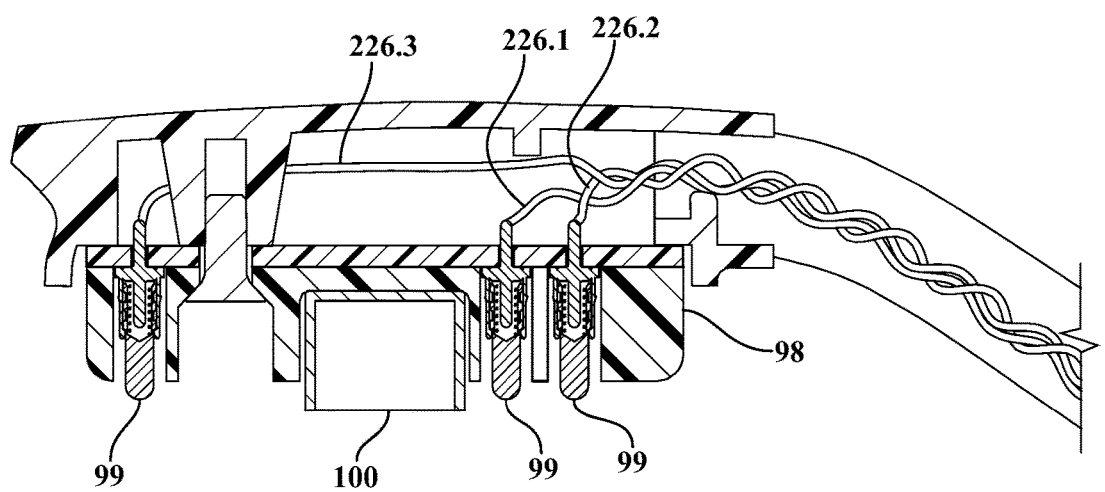
FIG. 8

AUSCULTATORY SOUND-OR-VIBRATION SENSOR

CROSS-REFERENCE TO RELATED APPLICATIONS

The instant application is a division of U.S. application Ser. No. 17/179,884 filed on 19 Feb. 2021, now U.S. Pat. No. 11,510,644, which is a division of U.S. application Ser. No. 16/152,004 filed on 4 Oct. 2018, now U.S. Pat. No. 10,925,573, which claims the benefit of U.S. Provisional Application Ser. No. 62/568,155 filed on 4 Oct. 2017. Each of the above-identified applications is incorporated herein by reference in its entirety.

BRIEF DESCRIPTION OF THE DRAWINGS

In the accompanying drawings:

FIG. 1B illustrates a fragmentary cross-sectional view of the first aspect of the auscultatory sound-or-vibration sensor illustrated in FIG. 1a;

FIG. 2 illustrates a sub-assembly of three of the first-aspect auscultatory sound-or-vibration sensors, each of which is in accordance with FIG. 1a;

FIG. 7a illustrates a side view of an auscultatory sound-or-vibration sensor and a plurality of human hairs adjacent thereto that are not encapsulated by a relatively-thin hydrogel or adhesive layer after placement of the auscultatory sound-or-vibration sensor on the thorax of the test subject, with the auscultatory sound-or-vibration sensor unperturbed by a lateral force;

FIG. 7b illustrates a side view of the auscultatory sound-or-vibration sensor and plurality of human hairs from FIG. 7a, but with the auscultatory sound-or-vibration sensor perturbed by a lateral force;

FIG. 8 illustrates a cross-sectional view of a connector and associated conductive leads, associated with a second aspect of an auscultatory sound-or-vibration sensor;

FIG. 9b illustrates a fragmentary cross-sectional view of the first embodiment of the second aspect of the auscultatory sound-or-vibration sensor illustrated in FIG. 9a;

FIG. 10 illustrates a top view of the second aspect of an auscultatory sound-or-vibration sensor illustrated in FIGS. 9a and 11a;

FIG. 11b illustrates a fragmentary cross-sectional view of the second embodiment of the second aspect of the auscultatory sound-or-vibration sensor illustrated in FIG. 11a;

FIG. 17b illustrates a fragmentary cross-sectional view of the third-aspect auscultatory sound-or-vibration sensor illustrated in FIG. 17a;

FIG. 20b illustrates a connector portion of a recording module that provides for mating with the connector portion of the wiring harness illustrated in FIGS. 18, 19 and 20a;

DESCRIPTION OF EMBODIMENT(S)

Figure 1A:
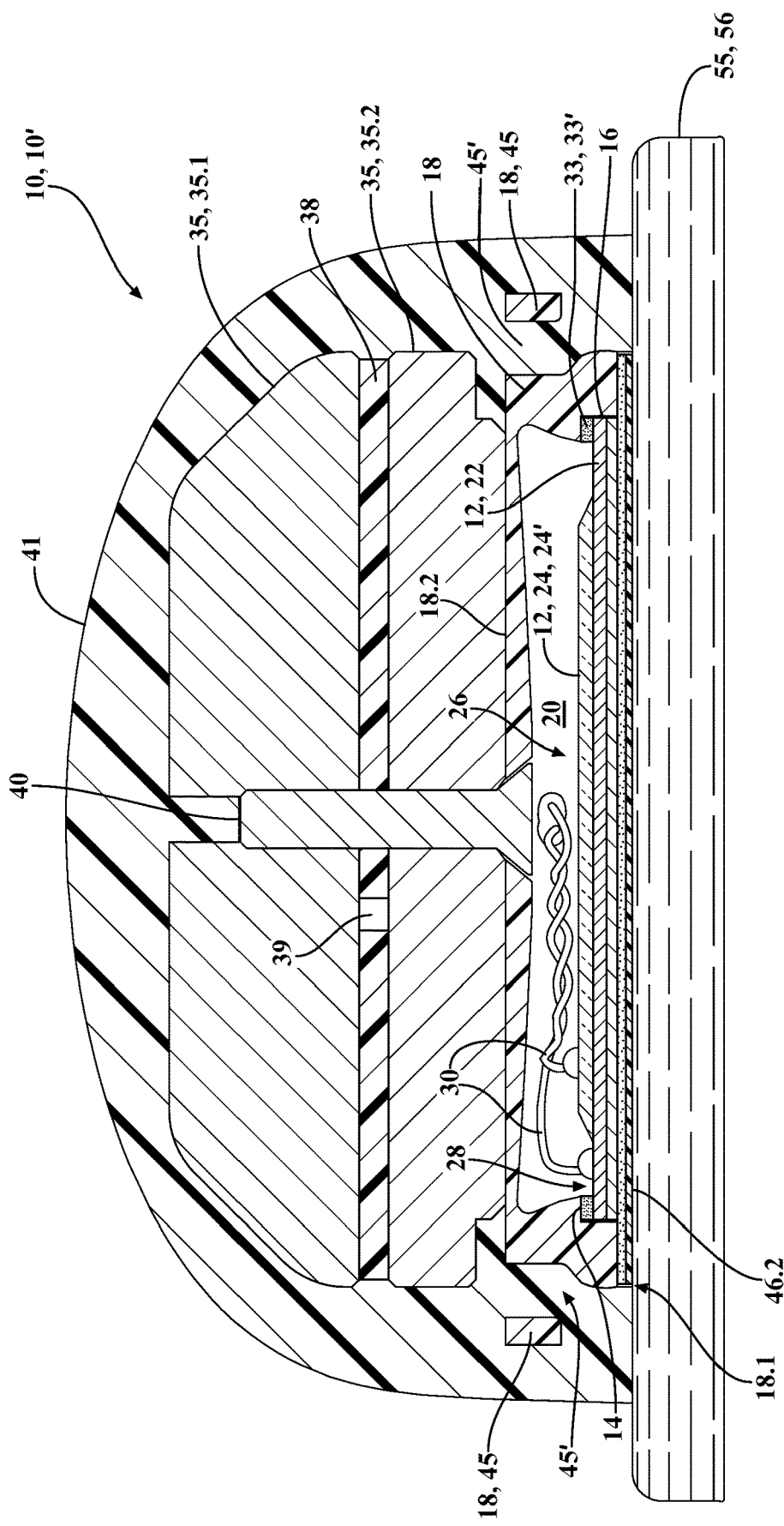
FIG. 1a illustrates a cross-sectional view of a first aspect of an auscultatory sound-or-vibration sensor.
Figure 1B:
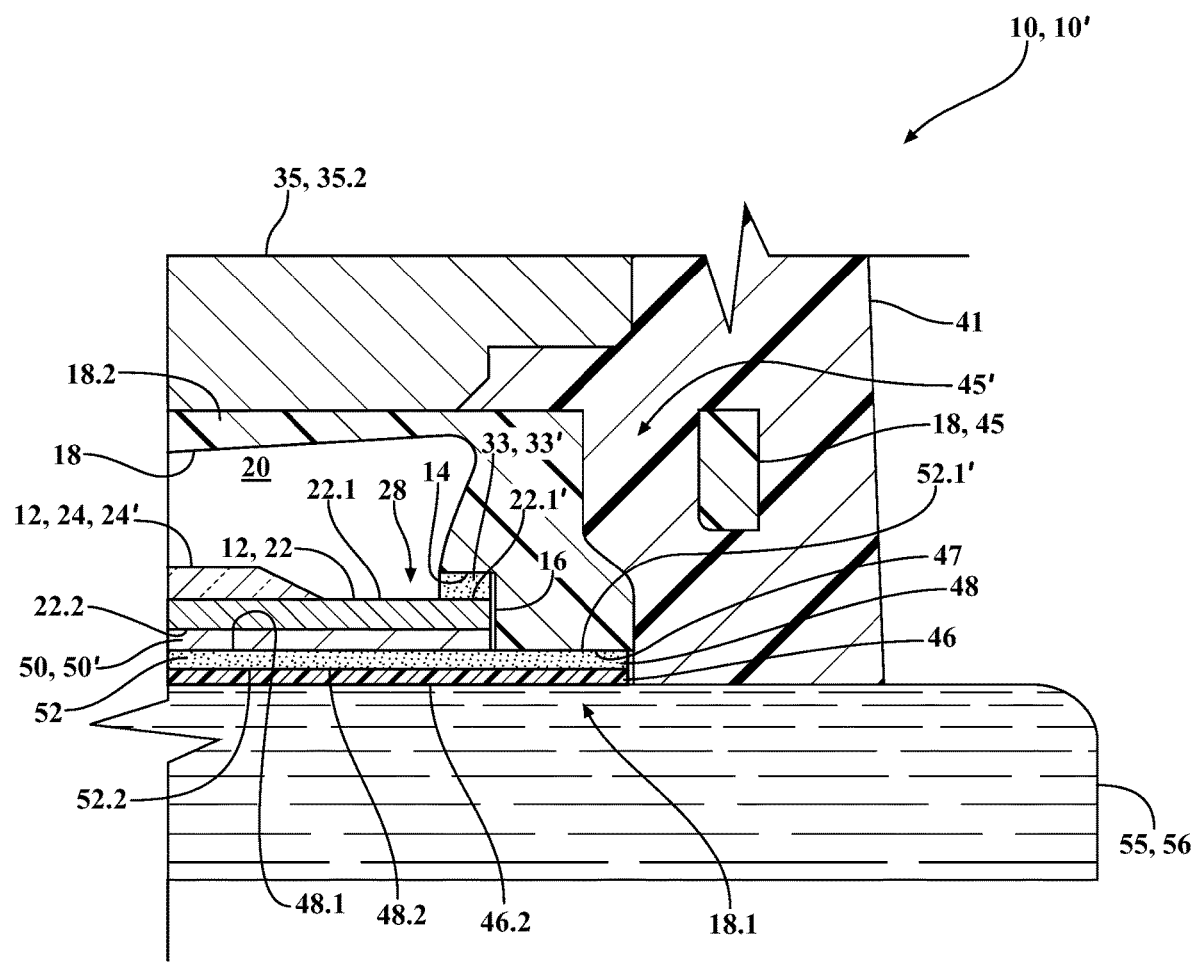

Referring to FIGS. 1-4, a first aspect 10' of an auscultatory sound-or-vibration sensor 10, 10' incorporates a piezoelectric sensor disk 12 that is adhesively bonded to a base rim 14 of a relatively shallow counterbore 16 in an open end 18.1 of an open-ended hollow housing 18, so as to close the open-ended hollow housing 18, thereby forming a cavity 20 therewithin. For example, in one set of embodiments, the hollow housing 18 is 3-D printed from polylactic acid (PLA), but alternatively could be made of any rigid plastic, for example, acrylic, acrylonitrile butadiene styrene (ABS) or Delrin®, for example by 3-D printing, injection molding or machining; or could be made from metal, for example, aluminum, brass, steel that is machined or cast, or a powdered metal composition that could be either sintered or additively manufactured.

As used herein, the terms "auscultatory sound" and "auscultatory sound or vibration" are each intended to mean a sound or vibration originating from inside a human or animal organism as a result of the biological functioning thereof, for example, as might be generated by action of the heart, lungs, other organs, or the associated vascular system; and is not intended to be limited to a particular range of frequencies—for example, not limited to a range of frequencies or sound/vibration intensities that would be audible to a human ear,—but could include frequencies above, below, and in the audible range, and sound/vibration intensities that are too faint to be audible to a human ear. Furthermore, the terms "auscultatory-sound sensor" and "auscultatory sound-or-vibration sensor" are each intended to mean a sound or vibration sensor that provides for transducing auscultatory sounds or vibrations into a corresponding electrical or optical signal that can be subsequently processed, and is not limited to a particular mode of transduction.

The piezoelectric sensor disk 12 comprises a metallic diaphragm disk substrate 22, for example, constructed of either brass, a nickel alloy, or stainless steel, to which is bonded a layer of piezoelectric material 24 within a relatively central region 26 of the metallic diaphragm disk substrate 22 on the surface 22.1 of the metallic diaphragm disk substrate 22 facing the cavity 20, leaving an outer annular region 28 of the metallic diaphragm disk substrate 22 exposed. For example, in one set of embodiments, the piezoelectric material 24 comprises a piezoelectric ceramic, for example, lead zirconate titanate (PZT) 24'. Alternatively, the piezoelectric material 24 could comprise either Lithium niobate (LiNbO3), Barium titanate, Lead titanate (PbTiO3), or Polyvinylidene fluoride (PVDF); the particular type of piezoelectric material is not limiting. In one set of embodiments, both the metallic diaphragm disk substrate 22 and the piezoelectric material 24, 24' are each about 0.1 mm thick. Generally, the resonant frequency of the metallic diaphragm disk substrate 22 is directly related to the associated thickness, that, for one manufacturer, can range between 0.1 mm and 1.3 mm for a metallic diaphragm disk substrate 22 constructed of brass. The resonant frequency is also responsive to the type of associated material. For example, the metallic diaphragm disk substrate 22 might alternatively be constructed of stainless steel. A pair of conductive leads 30, respectively connected to the piezoelectric material 24 and the outer annular region 28 of the metallic diaphragm disk substrate 22, provide for transmitting an electrical signal from the piezoelectric material 24—generated thereby responsive to a sound-induced mechanical disturbance thereof—to an associated recording module 32 for subsequent processing and use, for example, in accordance with the teachings of the following: U.S. Provisional Application No. 62/560,568 filed on 19 Sep. 2017, entitled SYSTEM AND METHOD FOR DETECTING DECOUPLING OF AN AUSCULATORY SOUND SENSOR FROM A TEST-SUBJECT, U.S. patent application Ser. No. 16/136,015 filed on 19 Sep. 2018, entitled SYSTEM AND METHOD FOR DETECTING DECOUPLING OF AN AUSCULTATORY SOUND SENSOR FROM A TEST-SUBJECT; U.S. Provisional Application No. 62/575,364 filed on 20 Oct. 2017, entitled CORONARY ARTERY DISEASE DETECTION SYSTEM, U.S. Provisional Application No. 62/575,383 filed on 21 Oct. 2017, entitled SYSTEM AND METHOD FOR PROCESSING AUSCULTATORY SOUND SIGNALS OF A CORONARY-ARTERY-DISEASE DETECTION SYSTEM, U.S. Provisional Application No. 62/575,390 filed on 21 Oct. 2017, entitled METHOD OF SCREENING AUSCULTATORY SOUND SIGNALS, and U.S. Provisional Application No. 62/575,397 filed on 21 Oct. 2017, entitled METHOD OF DETECTING CORONARY ARTERY DISEASE, each of which is incorporated by reference herein in its entirety. In operation of the auscultatory sound-or-vibration sensor 10, a sound-or-vibration-induced mechanical vibration of the metallic diaphragm disk substrate 22 induces associated mechanical stresses in the piezoelectric material 24 that, in turn, generates a voltage responsive thereto that is transmitted to the recording module 32 by the pair of conductive leads 30.

The outer edge portion 22.1' of the cavity-facing surface 22.1 of the metallic diaphragm disk substrate 22 is adhesively bonded to the base rim 14 of the counterbore 16 in the open end 18.1 of the hollow housing 18 with a flexible adhesive 33 that provides for a flexible connection therebetween that readily accommodates sound-or-vibration-induced vibration of the metallic diaphragm disk substrate 22 without degradation of the associated adhesive bond, which effectively provides for the metallic diaphragm disk substrate 22 to "float" relative to the hollow housing 18. For example, in one set of embodiments, the flexible adhesive 33 comprises an annular ring of double-sided acrylic adhesive tape 33', for example, that is cut from LIC-913 double-sided acrylic tape, which provides for consistent and repeatable performance from one sensor to another. Alternatively, the flexible adhesive 33 could comprise silicone RTV; a flexible polyurethane sealant, for example, SikaFlex®; a thermosetting contact adhesive with solid contents of pigment reinforced synthetic rubber and synthetic plastic resin sold under the trade name Pliobond®; or a flexible cyano-acrylate glue, for example, Loctite® 4902. This edge mounting of the metallic diaphragm disk substrate 22 provides for the relatively lowest resonant frequency for a given diameter thereof, and the relatively highest sensitivity, in comparison with other mounting configurations. The outer diameter of the metallic diaphragm disk substrate 22 is sufficiently small—for example, in one set of embodiments, 27 mm in diameter, for example, as used in commercial buzzers—so as to provide for targeting, with particularity, particular intercostal spaces of the associated test subject 34 being tested. Commercially-available piezoelectric sensor disks 12 are sometimes referred to as "piezoelectric benders".

Figure 4:
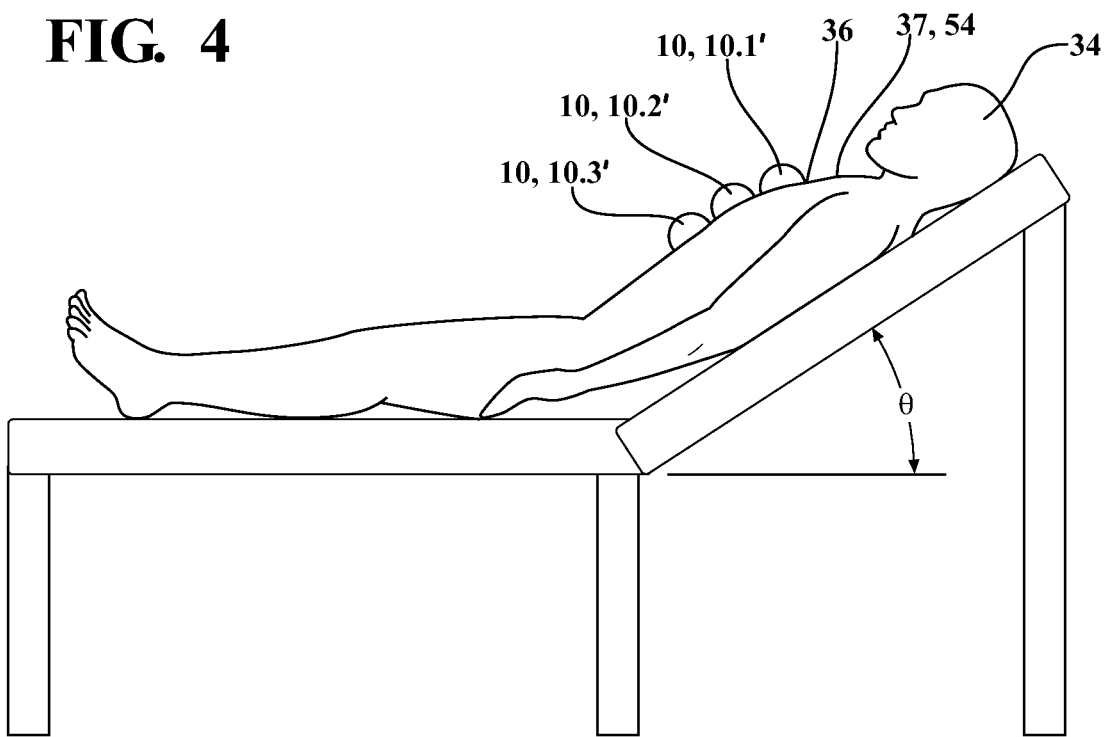
FIG. 4 illustrates a test subject reclined on a surface, with their torso inclined while capturing auscultatory sound-or-vibration signals from a plurality of auscultatory sound-or-vibration sensors attached to the thorax of the test subject.

The auscultatory sound-or-vibration sensor 10, 10' further incorporates one or more inertial masses 35, 35.1, 35.2 abutting the outside of the closed end 18.2 of the hollow housing 18, which provide sufficient mass to hold the auscultatory sound-or-vibration sensor 10, 10' against the skin 36 of the thorax 37 of the test subject 34 with a sufficient bias force so that the auscultatory sounds or vibrations of the test subject 34 are detectable by the piezoelectric sensor disk 12, and, in cooperation with the below-described acoustically-transmissible-adhesive interface 55, for example, the below-described layer of hydrogel material 55, 56, to provide for sufficient adhesion to the skin 36 of the thorax 37 of the test subject 34 so as to retain the auscultatory sound-or-vibration sensor 10, 10' on the skin 36 of the thorax 37 of the test subject 34 during a test, with the torso 54 of the test subject 34 at an inclination angle 19, for example, in one embodiment, at about 30 degrees above horizontal, as illustrated in FIG. 4. Although, in one set of embodiments, the inertial masses 35, 35.1, 35.2 are constructed of brass, the particular material thereof is not limiting. In one set of embodiments, the auscultatory sound-or-vibration sensor 10, 10' incorporates first 35.1 and second 35.2 inertial masses separated by a spacer 38, for example, made of plastic, incorporating one or more passages 39 therealong through which one or more electrical cables with associated pairs of conductive leads 30, or a strain-relief cable, may be routed when interconnecting two or more auscultatory sound-or-vibration sensors 10, 10' to one another. In accordance with one set of embodiments, the first 35.1 and second 35.2 inertial masses are secured to one another—with the spacer 38 sandwiched therebetween—and to the closed end 18.2 of the hollow housing 18 with a flat-headed machine screw 40 inserted through the closed end 18.2 of the hollow housing 18 from the cavity 20, that is screwed into the second inertial mass 35.2, passes through the spacer 38, and upon which is screwed the first inertial mass 35.1.

Figure 2:
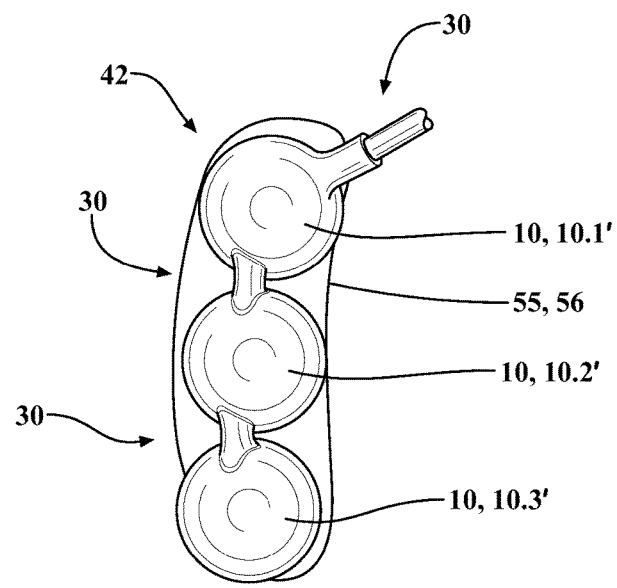
Figure 3:
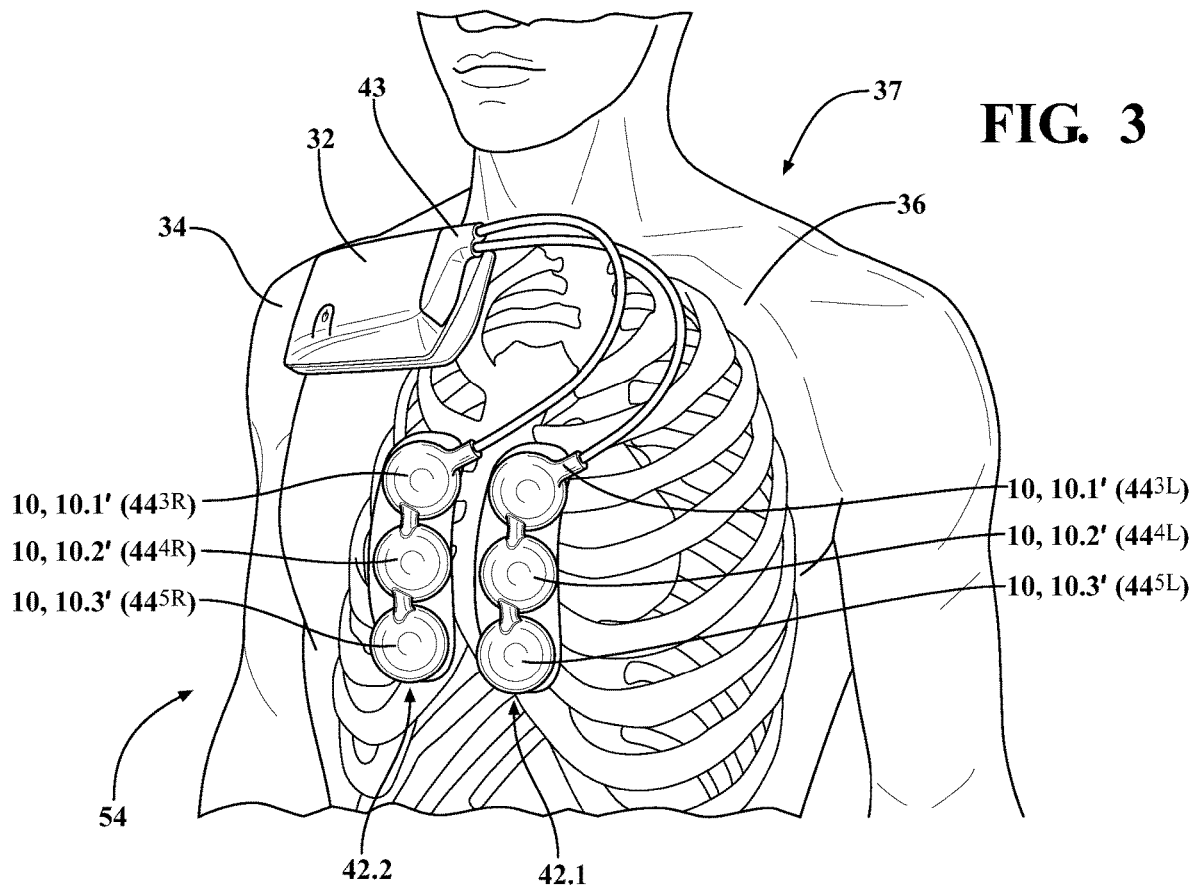
FIG. 3 illustrates two sub-assemblies—each consisting of three of the first-aspect auscultatory sound-or-vibration sensors—located on the torso of a test subject at the right and left, third, fourth and fifth, intercostal spaces in relation to the ribs and heart of the test subject, each sub-assembly operatively coupled to an electrical connector that provides for connection to an associated recording module.

The auscultatory sound-or-vibration sensor 10, 10' is formed by overmolding a sub-assembly of the hollow housing 18 and inertial mass(es) 35, 35.1, 35.2 with a layer of relatively compliant overmolding material 41, the latter of which provides for dampening external sounds and which provides for an improved tactile feel for to the operator. Furthermore, as illustrated in FIGS. 2 and 3, in one set of embodiments, a sensor assembly 42 can be formed by simultaneously overmolding three auscultatory sound-or-vibration sensors 10, 10.1', 10.2', 10.3' with the overmolding material 41, wherein the associated pairs of conductive leads 30 from each auscultatory sound-or-vibration sensor 10, 10.1', 10.2', 10.3' are connected to an associated electrical connector 43, the latter of which provides for operatively coupling the auscultatory sound-or-vibration sensors 10, 10.1', 10.2', 10.3' to the recording module 32. For example, in one set of embodiments, the electrical connector 43 is connected to two such sensor assemblies 42, 42.1, 42.2, and can be releasably attached to the recording module 32 by a magnetic attraction therebetween, wherein associated electrical contacts are provided for by a plurality of spring-loaded POGO®-style contacts, one for each conductor of each signal channel to be connected. For example, each pair of conductive leads 30 associated with a given auscultatory sound-or-vibration sensor 10, 10' associated with a corresponding signal channel would utilize two such POGO®-style contacts—one for each lead—and possibly a third contact for a corresponding shield if the pair of conductive leads 30 was shielded. Similarly, a below-described ECG electrode would use a POGO®-style contact for each ECG electrode, and possibly one or more additional POGO®-style contacts for a corresponding one or more associated shields. The auscultatory sound-or-vibration sensors 10, 10.1', 10.2', 10.3' of each sensor assembly 42 are in a daisy-chain arrangement, with the individual auscultatory sound-or-vibration sensors 10, 10.1', 10.2', 10.3' separated from one another by sufficient distances so as to provide for being respectively located, for example, above the third $44^{3L}$, $44^{3R}$, fourth $44^{4L}$, $44^{4R}$ and fifth $44^{5L}$, $44^{5R}$, intercostal spaces on the left and right side of the test subject 34, respectively, for the first 42.1 and second 42.2 sensor assemblies, respectively, or more generally, but not limited to, a set of three intercostal spaces—for example, ranging from the second to the fifth—at two different lateral locations—for example, two of the left (L), sternum (S) and right (R) lateral locations on the test subject 34. For example, the pair of conductive leads 30 from the third auscultatory sound-or-vibration sensor 10, 10.3'—most distant from the electrical connector 43—are routed to the electrical connector 43 through the passages 39 in the spacers 38 of the second 10, 10.2' and first 10, 10.1' auscultatory sound-or-vibration sensors, and the pair of conductive leads 30 from the second auscultatory sound-or-vibration sensor 10, 10.2'—located between the second 10, 10.2' and first 10, 10.1' auscultatory sound-or-vibration sensors—is routed to the electrical connector 43 through the passage 39 in the spacer 38 of the first auscultatory sound-or-vibration sensor 10, 10.1'. The entire sensor assembly 42—including the auscultatory sound-or-vibration sensors 10, 10.1', 10.2', 10.3' and the pairs of conductive leads 30 passing therebetween—is overmolded, for example, with a silicone rubber overmolding material 41, for example, Ecoflex® Shore 00-30 Silicone manufactured by Smooth-On, Inc. In one set of embodiments, the hollow housings 18 of the auscultatory sound-or-vibration sensors 10, 10' each incorporate an external flange 45, for example, incorporating a plurality of holes 45' therein, that provides for retaining the auscultatory sound-or-vibration sensors 10, 10' within the cured overmolding material 41.

Referring again to FIG. 1, the open end 18.1 of the hollow housing 18 is covered with a plastic-film layer 46—for example, polyester or mylar—that is adhesively bonded to the outer rim 47 of the open end 18.1 of the hollow housing 18, and placed over the outwardly-facing surface 22.2 of the metallic diaphragm disk substrate 22 of the piezoelectric sensor disk 12. More particularly, in one set of embodiments, a 3 mil thick plastic-film layer 46 is adhesively bonded with a double-sided adhesive tape 48, for example, 3M® 468MP adhesive transfer tape comprising a 5 mil thick acrylic adhesive on a polycoated kraft paper liner 50, wherein on the cavity-facing side 48.1 of the double-sided adhesive tape 48, an annular ring 52.1' of adhesive 52 of the double-sided adhesive tape 48 is exposed by removal of a corresponding portion of the associated paper liner, leaving a remaining central portion 50' of the associated paper liner 50—which shadows the piezoelectric sensor disk 12—attached to the adhesive 52 on the cavity-facing side 48.1 of the double-sided adhesive tape 48, so as to be free to slide relative to the piezoelectric sensor disk 12, and thereby not otherwise adversely reduce the sensitivity thereof to auscultatory-sound-or-vibration-induced vibration The plastic-film layer 46 is adhesively bonded to the outwardly-facing surface 52.2 of the adhesive 52 of the double-sided adhesive tape 48 after removal of the associated paper liner from the outwardly-facing side 48.2 thereof.

Referring to FIG. 4, it has been found that the quality of the auscultatory sound-or-vibration signals acquired from a test subject 34 can be improved if the torso 54 of the test subject 34 is at an inclination angle θ of about 30 degrees above horizontal—but generally, as close to upright (i.e. θ=90 degrees) as can be accommodated by an associated adhesive interface 55 of the associated auscultatory sound-or-vibration sensors 10, $10^{1'}$, $10^{2'}$, $10^{3'}$ that provides for attachment thereof to the skin 36 of the test subject 34 —, which imposes a transverse component of gravitational force on the auscultatory sound-or-vibration sensors 10, 10.1', 10.2', 10.3' that is resisted by the associated adhesive interface 55. Furthermore, the auscultatory sound or vibration signals acquired from a test subject 34 can also be improved by acoustically coupling the auscultatory sound-or-vibration sensors 10, 10.1', 10.2', 10.3' to the skin 36 of the thorax 37 of the test subject 34, for example, with an acoustically-transmissive medium in intimate contact with the skin 36 and having an acoustic impedance similar thereto. Although a typical ultrasound gel would work with the test subject 34 in a level position, this gel does not provide for sufficient shear resistance to prevent the auscultatory sound-or-vibration sensors 10, 10.1', 10.2', 10.3' from sliding over the skin 36, absent an external means—for example, a flexibly coupled overhead support—for doing so. Accordingly, a layer of hydrogel material 55, 56, for example, in one set of embodiments, a 1.2 mm thick P-DERM® hydrogel sold by Polymer Science, Inc., identified as PS-1446-1.2—comprising a hydrophilic polymer matrix with a high water content—provides for securing the auscultatory sound-or-vibration sensors 10, 10.1', 10.2', 10.3' to the skin 36 of the thorax 37 of the test subject 34, and provides for retaining the position thereof for the duration of the test. The hydrogel material 55, 56 has sufficient bond, tackiness and hair-wetting properties to provide for good attachment and coupling both to the outwardly-facing surface 46.2 of the plastic-film layer 46 of the auscultatory sound-or-vibration sensors 10, 10.1', 10.2', 10.3', and to the skin 36, while allowing pain-free removal from the skin 36. The plastic-film layer 46 provides for transmitting shear forces directly to the hollow housing 18 from the layer of hydrogel material 55, 56 during installation and removal, thereby isolating the piezoelectric sensor disk 12 from these forces, so as to protect the adhesive bond between the piezoelectric sensor disk 12 and the hollow housing 18.

Figure 5A:
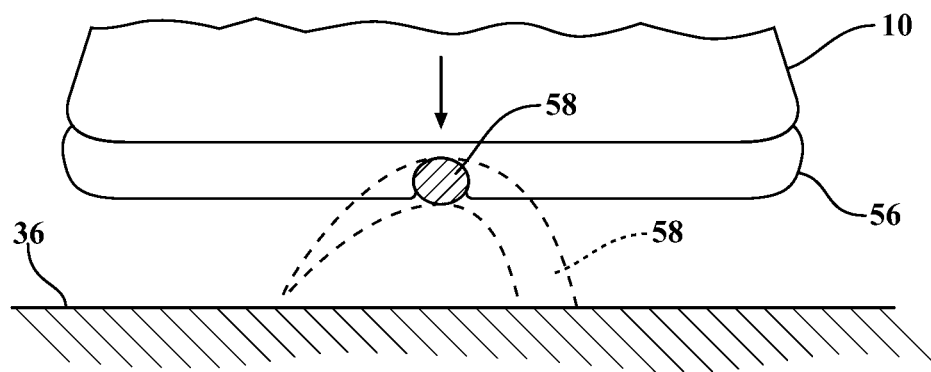
FIG. 5a illustrates a human hair interacting with a hydrogel layer that is used to attach a auscultatory sound-or-vibration sensor to the thorax of a test subject.
Figure 5B:
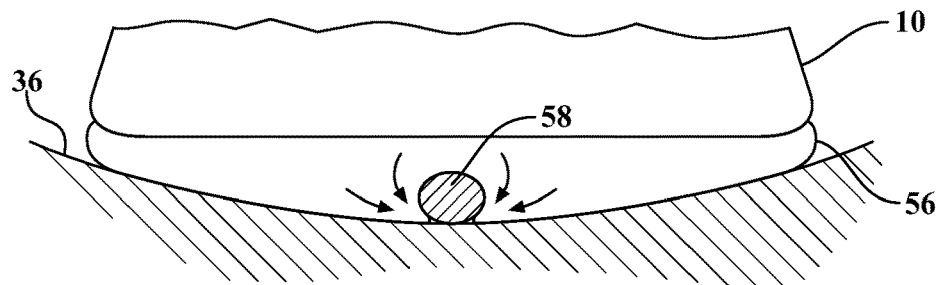
FIG. 5b illustrates a cross-sectional view of the human hair illustrated in FIG. 5a, encapsulated by the hydrogel layer during placement of the auscultatory sound-or-vibration sensor on the thorax of the test subject as the auscultatory sound-or-vibration sensor is pressed onto the skin.
Figure 5C:
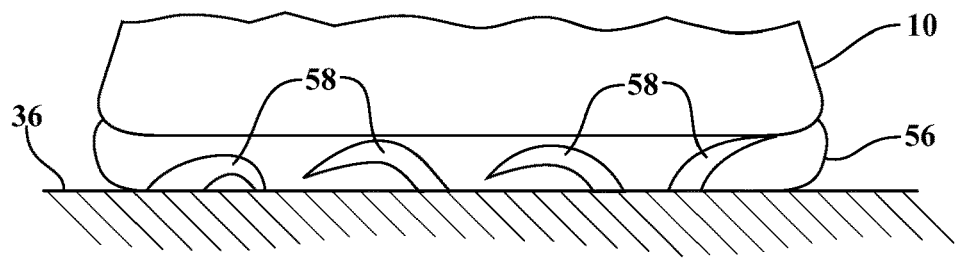
FIG. 5c illustrates a side view of a plurality of human hairs encapsulated by a hydrogel layer after placement of the auscultatory sound-or-vibration sensor on the skin of the thorax of the test subject, and after chasing air out of the interface therebetween.

Referring to FIGS. 5a and 5b, when applied carefully to the skin 36 of the thorax 37 of the test subject 34 so as to not entrain air bubbles, the hydrogel material 56 encapsulates hairs 58 in the process of reaching the skin 36 therebeneath. The attachment to the skin 36 will be very good provided that there are no wrinkles that would otherwise provide for air to enter the center of the patch of hydrogel material 56. Removal has been found to be easy and painless provided that this is done sufficiently slowly so as to provide for a gradual separation from the skin 36 at a rate that is sufficiently slow so as to enable the hydrogel material 56 to flow around the hairs 58. Referring to FIG. 5c, a 1.2 mm thickness of the hydrogel material 56 in combination with the associated softness thereof is sufficient to provide for filling in minor gaps between the plastic-film layer 46 and the skin 36, and makes the hydrogel material 56 less prone to wrinkling. Referring to FIGS. 5b and 5c, the hydrogel material 56 fills in the interstices between hairs 58 as the auscultatory sound-or-vibration sensors 10, 10.1', 10.2', 10.3' are pressed onto the skin 36, provides a good acoustic coupling between the skin 36 and the plastic-film layers 46 of the auscultatory sound-or-vibration sensors 10, 10.1', 10.2', 10.3' without associated residual stresses within the hydrogel material 56, and prevents the hairs 58 from rubbing against each other and against the skin 36, the latter of which otherwise might cause acoustic noise. Sounds or vibrations of or from the test subject 34 coupled through the hydrogel material 56 to the plastic-film layers 46 of the auscultatory sound-or-vibration sensors 10, 10.1', 10.2', 10.3' are further coupled through the adhesive 52 of the double-sided adhesive tape 48, then through the central portion 52' of the associated paper liner 50, and onto the metallic diaphragm disk substrate 22 of the piezoelectric sensor disk 12, causing an associated vibration thereof, resulting in a corresponding acoustically-caused electrical signal that is transmitted to the electrical connector 43 over the corresponding pair of conductive leads 30, for transmission to the recording module 32.

Figure 6A:
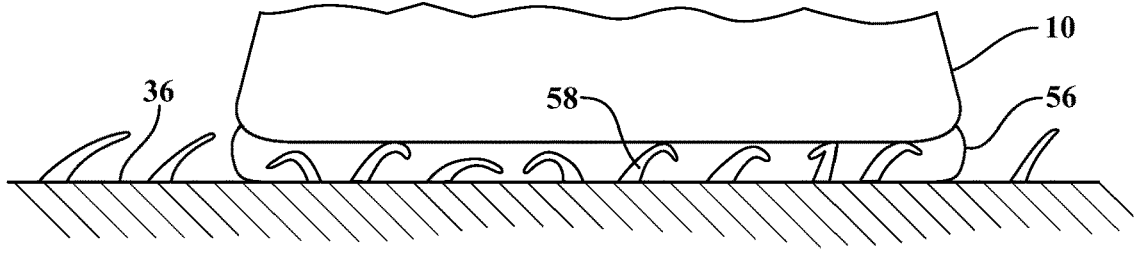
FIG. 6a illustrates a side view of an auscultatory sound-or-vibration sensor and a plurality of human hairs adjacent thereto that are encapsulated by an associated hydrogel layer after placement of the auscultatory sound-or-vibration sensor on the thorax of the test subject, with the auscultatory sound-or-vibration sensor unperturbed by a lateral force, wherein the hydrogel layer is sufficiently thick to fully encapsulate all of the hairs within the footprint of the auscultatory sound-or-vibration sensor.
Figure 6B:
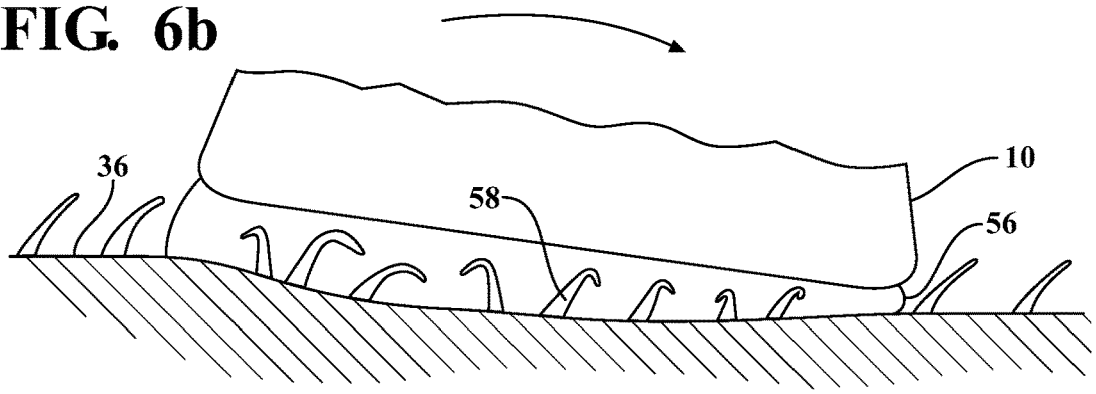
FIG. 6b illustrates a side view of the auscultatory sound-or-vibration sensor and plurality of human hairs from FIG. 6a, but with the auscultatory sound-or-vibration sensor perturbed by a lateral force.

Referring to FIGS. 6a and 6b, a sufficiently thick hydrogel material 56 attaching the auscultatory sound-or-vibration sensors 10, 10.1', 10.2', 10.3' to the skin 36 provides for the elimination of air gaps therewithin, and provides for encapsulating hairs 58 therebetween, resulting in an acoustic interface between the auscultatory sound-or-vibration sensors 10, 10.1', 10.2', 10.3' and the skin 36 that substantially matches the acoustic impedance of the skin 36; and that provides for resisting internal shear forces resulting from a transverse force applied to the auscultatory sound-or-vibration sensors 10, 10.1', 10.2', 10.3', wherein the resulting forces applied to the hydrogel material 56 causes a redistribution of the water content thereof that prevents a debonding thereof from the skin 36.

Referring to FIGS. 7a and 7b, an insufficiently thick hydrogel material 56 or a relatively-thin adhesive layer does not provide for fully encapsulating the hairs 58 therebeneath, so that the hydrogel material 56 does not fully bond to the skin 36. Accordingly, when exposed to an external force, the portions of the skin 36 that are bonded to the hydrogel material 56 may be subject to tension that is sufficient to cause a sudden release of a localized bond, which may result in an associated popping noise 60 that might be sensed by one or more of the auscultatory sound-or-vibration sensors 10, 10.1', 10.2', 10.3'.

For example, a layer of hydrogel material 56 having a thickness of about a half millimeter did not appear to be sufficiently thick to fully encapsulate the hairs 58 and fully bond to the skin 36—as otherwise illustrated in FIGS. 6a and 6b—so that that the thickness of the hydrogel material 56 would typically need to be greater than 0.5 mm unless there was no hair 58.

Figure 9A:
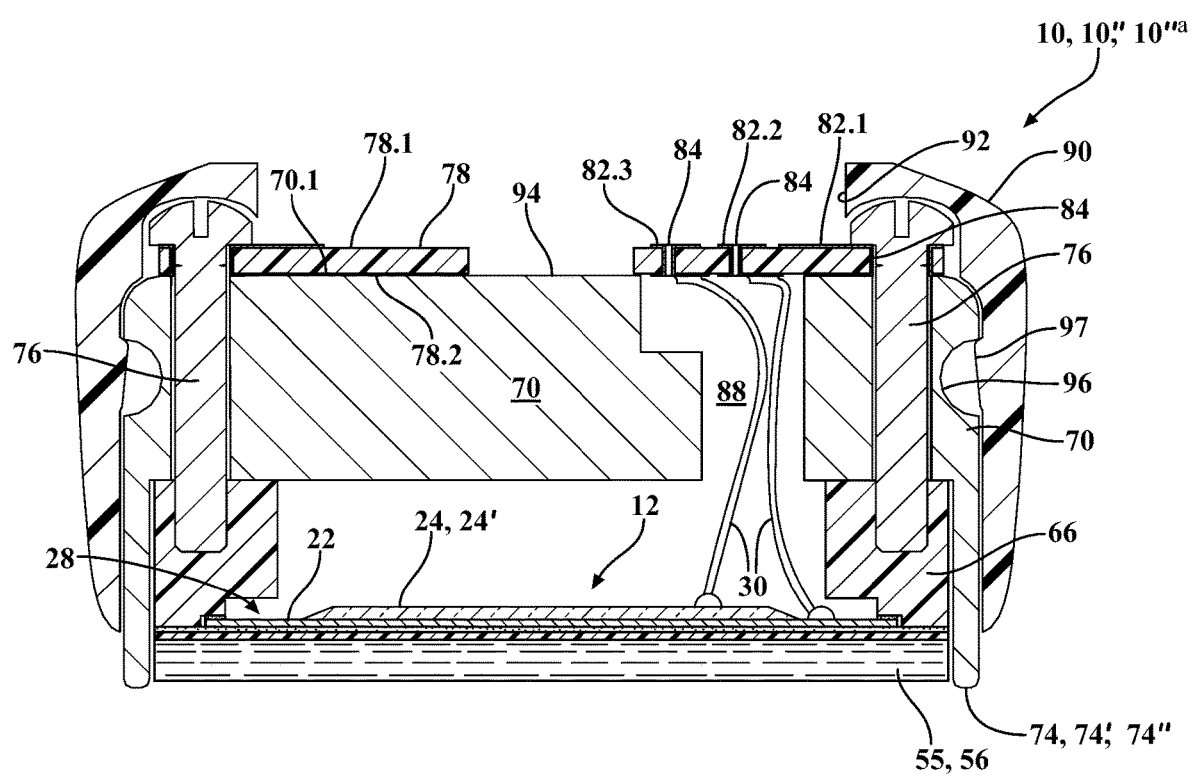
FIG. 9a illustrates a cross-sectional view of a first embodiment of the second aspect of an auscultatory sound-or-vibration sensor.
Figure 9B:
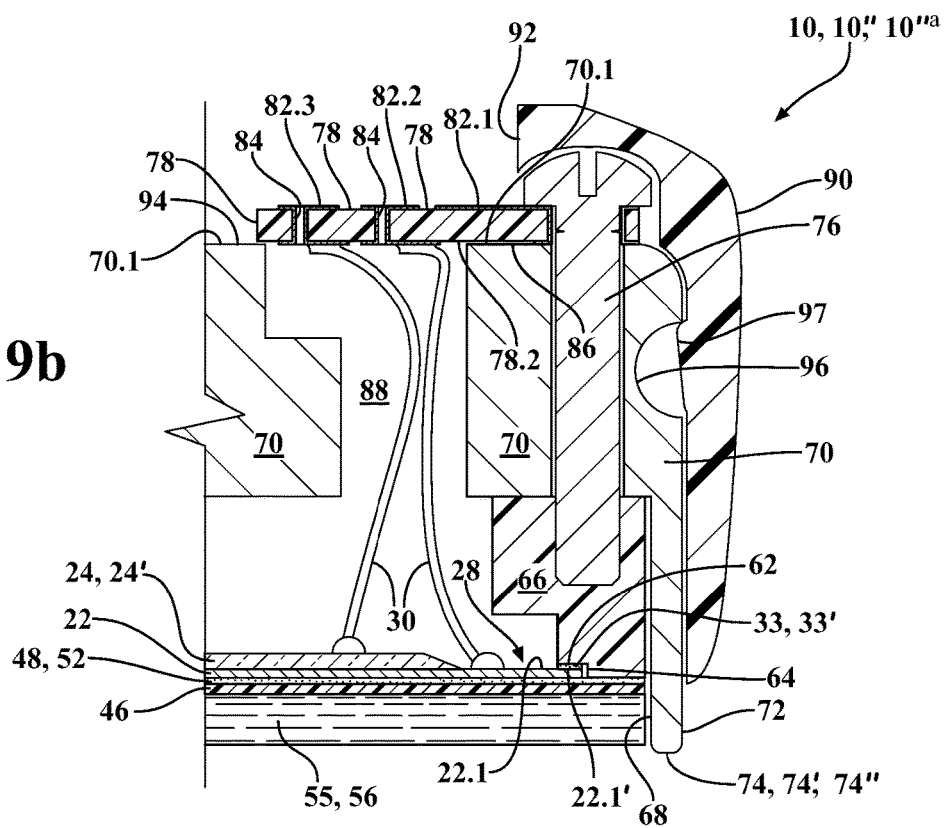
Figure 10:
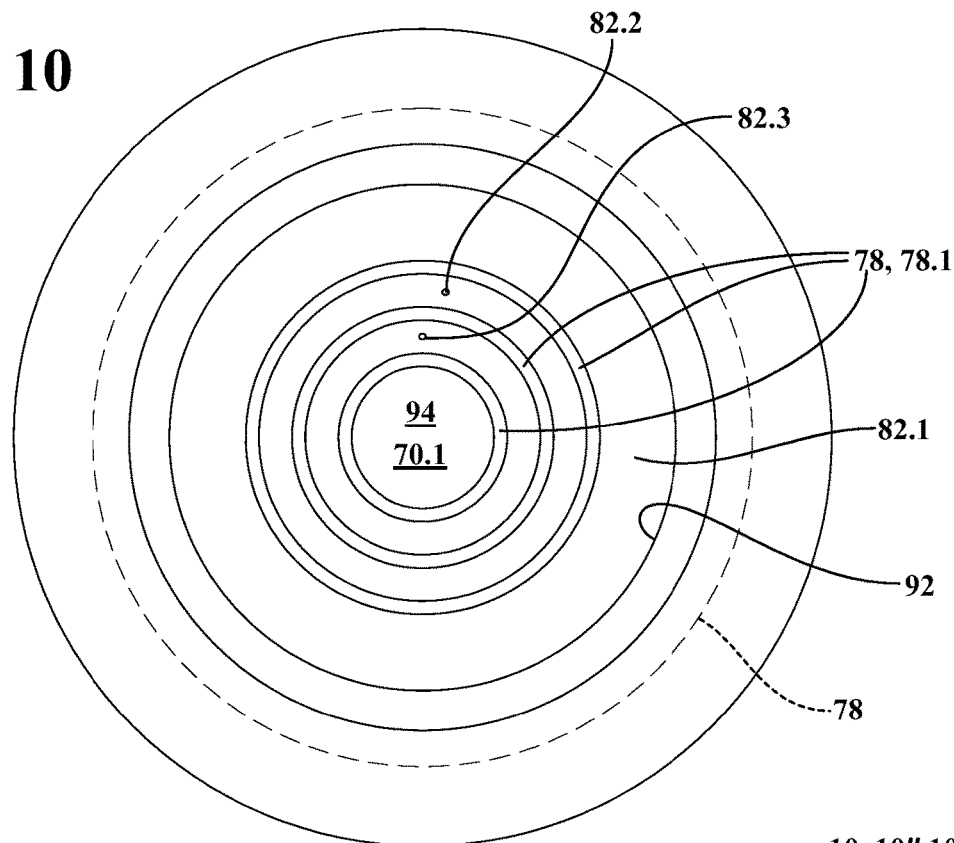
Figure 11A:
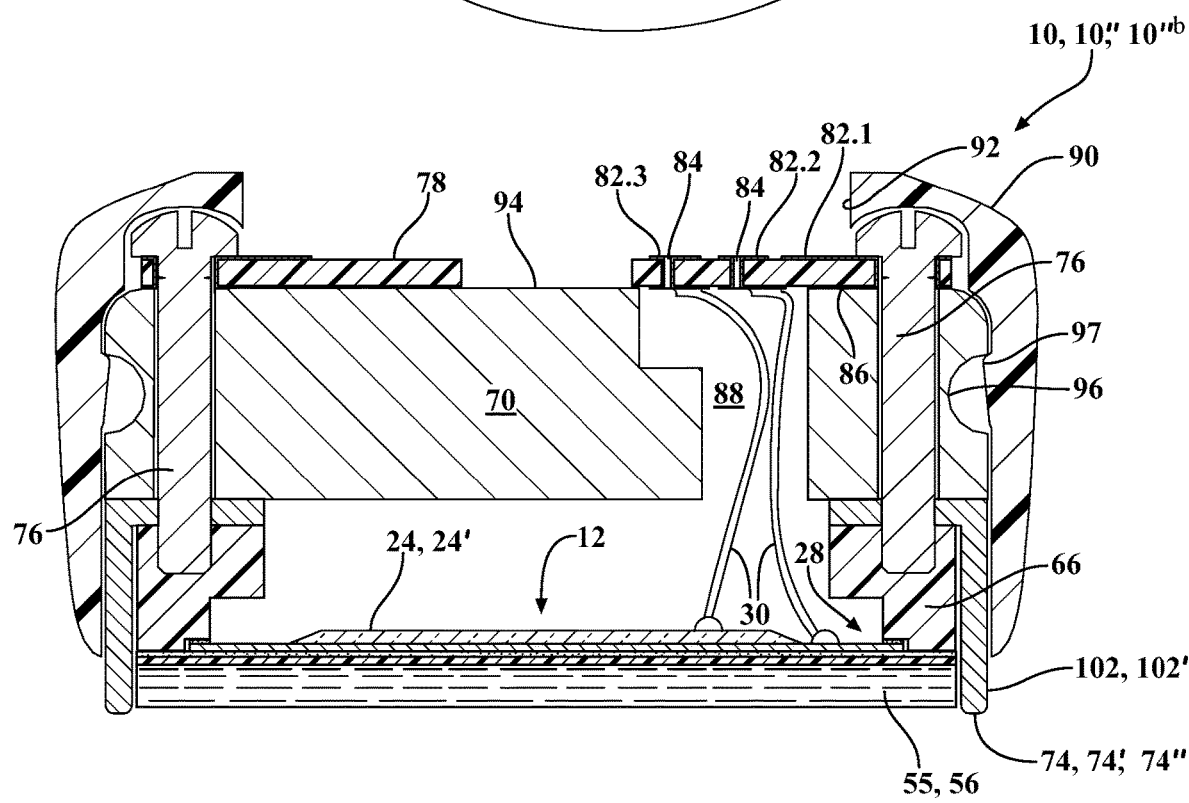
FIG. 11a illustrates a cross-sectional view of a second embodiment of the second aspect of an auscultatory sound-or-vibration sensor.
Figure 11B:
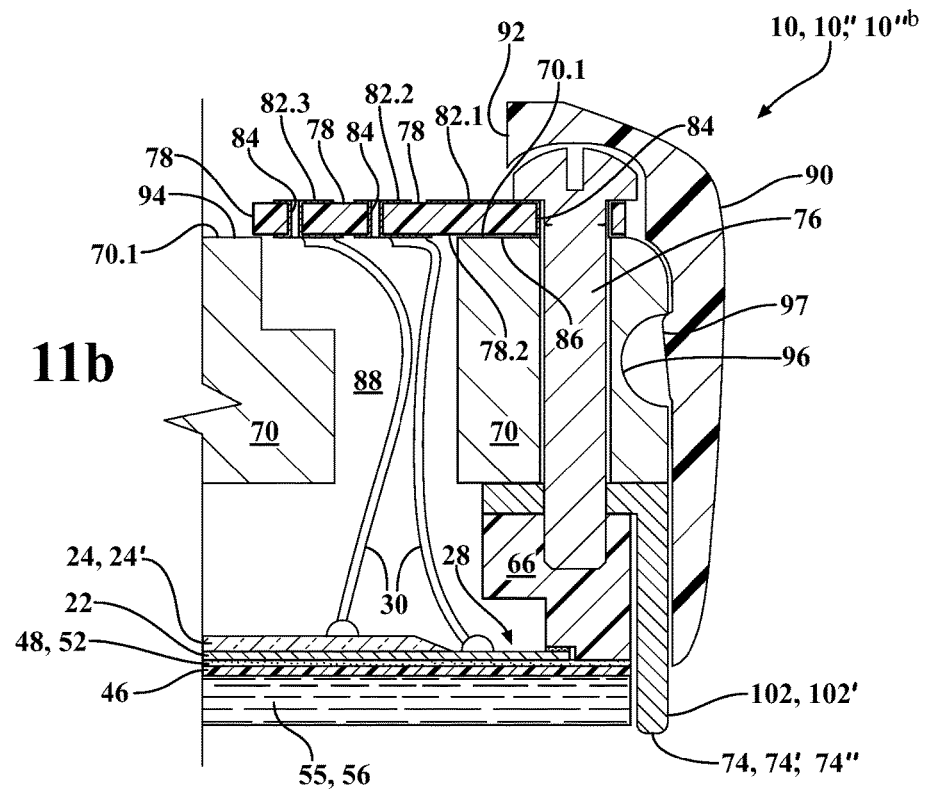

Referring to FIGS. 8-10, a first embodiment of a second aspect 10" of an auscultatory sound-or-vibration sensor 10, 10"$^a$ incorporates a piezoelectric sensor disk 12—the same as that described hereinabove for the first aspect 10'—that is adhesively bonded to a base rim 62 of a relatively shallow first counterbore 64 of a non-metallic bushing 66 that is installed in a second counterbore 68 in the open end of a plated steel housing 70 constructed of magnetically-permeable steel that is plated with a corrosion-inhibiting conductive material, for example, zinc or gold, wherein the rim 72 of the second counterbore 68 extends axially beyond the non-metallic bushing 66 so as to define an electrode 74 that may be used as an ECG electrode 74', or an associated ECG body ground electrode 74". It should be noted that a first-aspect auscultatory sound-or-vibration sensor 10, 10' would incorporate a similar non-metallic bushing 66 to engage the piezoelectric sensor disk 12 if the associated hollow housing 18 were constructed of a conductive material.

The outer edge portion 22.1' of the cavity-facing surface 22.1 of the metallic diaphragm disk substrate 22 is adhesively bonded to the base rim 62 of the relatively shallow first counterbore 64 in the non-metallic bushing 66 with a flexible adhesive 33 providing for a flexible connection thereto that readily accommodates sound-or-vibration-induced vibration of the metallic diaphragm disk substrate 22 without degradation of the associated adhesive bond, which effectively provides for the metallic diaphragm disk substrate 22 to "float" relative to the hollow housing 18. For example, in one set of embodiments, the adhesive bond is made with an annular ring of double-sided acrylic adhesive tape 33', for example, that is cut from LIC-913 double-sided acrylic tape, which provides for consistent and repeatable performance from one sensor to another. Alternatively, the adhesive bond could be made with silicone RTV; a flexible polyurethane sealant, for example, SikaFlex®; a thermosetting contact adhesive with solid contents of pigment reinforced synthetic rubber and synthetic plastic resin sold under the trade name PlioBond®; or a flexible cyano-acrylate glue, for example, Loctite® 4902. This edge mounting of the metallic diaphragm disk substrate 22 provides for the relatively lowest resonant frequency for a given diameter thereof, and the relatively highest sensitivity, in comparison with other mounting configurations. The outer diameter of the metallic diaphragm disk substrate 22 is sufficiently small—for example, in one set of embodiments, 27 mm in diameter, for example, as used in commercial buzzers, and sometimes referred to as piezoelectric "benders"—so as to provide for targeting, with particularity, particular intercostal spaces of the associated test subject 34 being tested.

For example, in one set of embodiments, the non-metallic bushing 66 is constructed of any rigid plastic, for example, ABS, Delrin or polycarbonate. The non-metallic bushing 66 provides for insulating the metallic diaphragm disk substrate 22 of the piezoelectric sensor disk 12 from the plated steel housing 70, and therefore, from the associated electrode 74. The non-metallic bushing 66 is held in the second counterbore 68 by a plurality of machine screws 76 that are also used to retain a printed circuit board 78 against the top surface 70.1 of the plated steel housing 70. The printed circuit board 78 incorporates three concentric annular electrodes 82.1, 82.2, 82.3 on the top surface 78.1 thereof. The first, outermost electrode 82.1 is in electrical communication by one or more printed-circuit vias 84 with at least one annular conductive layer 86 on the bottom surface 78.2 of the printed circuit board 78, so as to provide for electrical communication of the first, outermost electrode 82.1 with the plated steel housing 70, and therefore with the associated electrode 74 thereof.

The plated steel housing 70 inherently provides for sufficient inertial mass to hold the auscultatory sound-or-vibration sensor 10, 10' against the skin 36 of the thorax 37 of the test subject 34 with a sufficient bias force so that the auscultatory sounds or vibrations of the test subject 34 are detectable by the piezoelectric sensor disk 12, and, in cooperation with the below-described layer of hydrogel material 55, 56,—or generally, a material providing for an acoustically-transmissible-adhesive interface 55—to provide for sufficient adhesion to the skin 36 of the thorax 37 of the test subject 34 so as to retain the auscultatory sound-or-vibration sensor 10, 10' on the skin 36 of the thorax 37 of the test subject 34 during a test, with the torso 54 of the test subject 34 at an inclination angle θ, for example, at about 30 degrees above horizontal, as illustrated in FIG. 4.

Each of the second 82.2 and third 82.3 annular electrodes are in electrical communication with corresponding associated printed-circuit vias 84 that provide for receiving a pair of conductive leads 30 that pass through an axial opening 88 in the plated steel housing 70, wherein the conductive leads 30 of the pair respectively connect to the piezoelectric material 24 and to the outer annular region 28 of the metallic diaphragm disk substrate 22, respectively.

Similar to the first aspect 10.1', a plastic-film layer 46 is adhesively bonded to the outwardly-facing surface 66.1 of the non-metallic bushing 66, and placed over the outwardly-facing surface 22.2 of the metallic diaphragm disk substrate 22 of the piezoelectric sensor disk 12, but which, as with the first aspect 10.1', is not bonded to the metallic diaphragm disk substrate 22. A disk of hydrogel material 55, 56—or generally, a material providing for an acoustically-transmissible-adhesive interface 55—is inserted within the second counterbore 68 in order to secure the auscultatory sound-or-vibration sensor 10, 10" to the skin 36 of the thorax 37 of the test subject 34, with the electrode 74 axially extending therebeyond so as to provide for conductive contact with the skin 36 of the thorax 37 of the test subject 34.

The plated steel housing 70 is ensheathed with an outer housing 90 that provides for a circular opening 92 at the top of the auscultatory sound-or-vibration sensor 10, 10" within which the three concentric annular electrodes 82.1, 82.2, 82.3 and a central target pad portion 94 of the plated steel housing 70 are exposed, wherein the plated steel housing 70 incorporates an external circumferential groove 96 that provides for retaining the outer housing 90 on the plated steel housing 70, for example, by cooperation of a plurality of internal tabs 97—for example, three equiangularly-spaced internal tabs 97—molded into the outer housing 90, that engage with the external circumferential groove 96 of the plated steel housing 70. For example, in one set of embodiments, the outer housing 90 is 3-D printed from polylactic acid (PLA), but alternatively could be made of any rigid plastic, for example, acrylic, acrylonitrile butadiene styrene (ABS) or Delrin®, for example by 3-D printing, injection molding or machining. The circular opening 92 is configured to receive a corresponding circularly-shaped second electrical connector 98 that incorporates a plurality of spring-loaded POGO®-style contacts 99, at least one for, and in alignment with, each of the three concentric annular electrodes 82.1, 82.2, 82.3 on the printed circuit board 78, so as to provide for communicating the signals from the piezoelectric sensor disk 12, and the electrode 74, to the electrical connector 43 that connects to the recording module 32. The second electrical connector 98 magnetically attaches to the auscultatory sound-or-vibration sensor 10, 10" with a central steel-jacketed pot magnet 100 incorporated in or on the second electrical connector 98, and configured to attach to the central target pad portion 94 of the plated steel housing 70, and thereby cause the associated POGO®-style contacts to engage the corresponding concentric annular electrodes 82.1, 82.2, 82.3.

Referring to FIGS. 8, 10 and 11a-b, a second embodiment of a second-aspect auscultatory sound-or-vibration sensor 10, 10", 10"$^b$ is the same as the above-described first embodiment 10"$^a$ except that the associated ECG electrode 74' or ECG body ground electrode 74" is provided for by a separate conductive ring 102, for example, a gold-plated brass ring 102', that is conductively connected to the above-described first, outermost electrode 82.1 by one or more of the associated machine screws 76, with a plurality of other machine screws 76 being used to assist in retaining the non-metallic bushing 66 to which the piezoelectric sensor disk 12 is adhesively bonded.

Figure 12A:
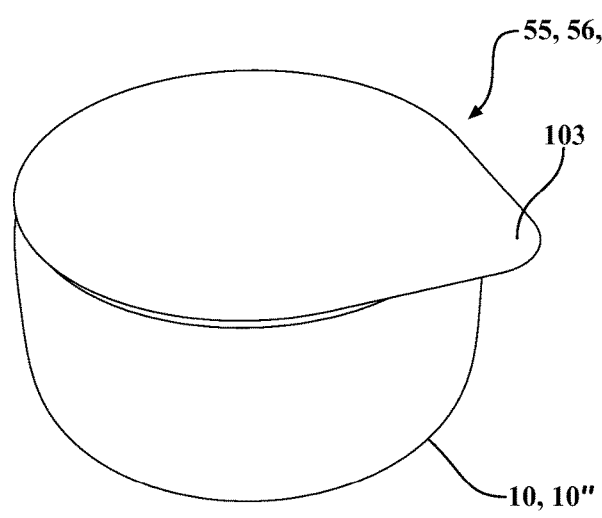
FIGS. 12a and 12b illustrate a second-aspect auscultatory sound-or-vibration sensor prior to attachment to a thorax of a test subject, respectively prior to and during removal of a liner that protects and adhesive surface of an associated acoustically-transmissible-adhesive interface.
Figure 12B:
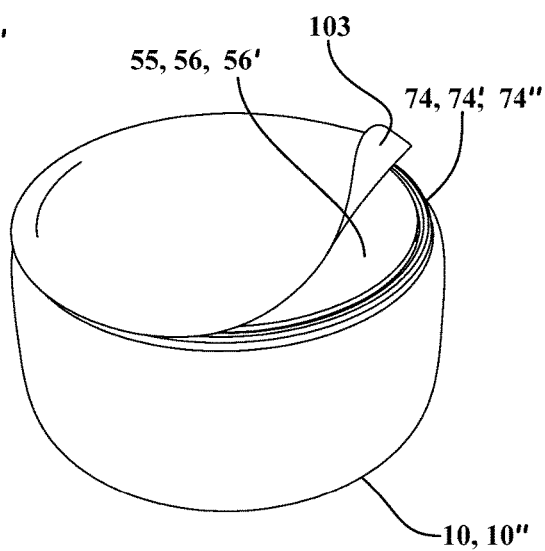
Figure 13:
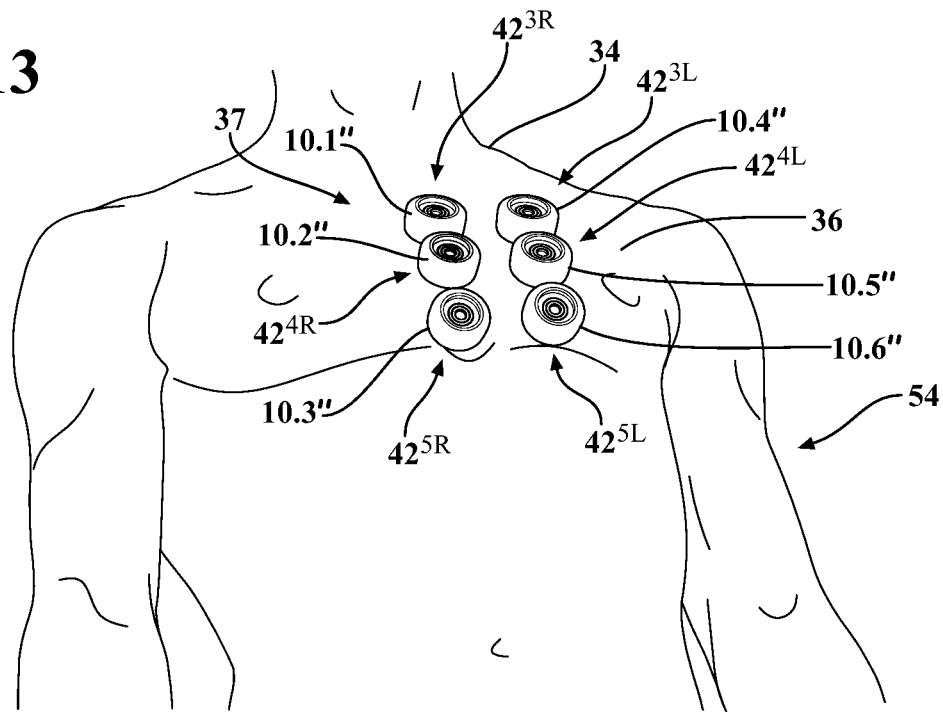
FIG. 13 illustrates a plurality of second-aspect auscultatory sound-or-vibration sensors attached to the thorax of the test subject.
Figure 14:
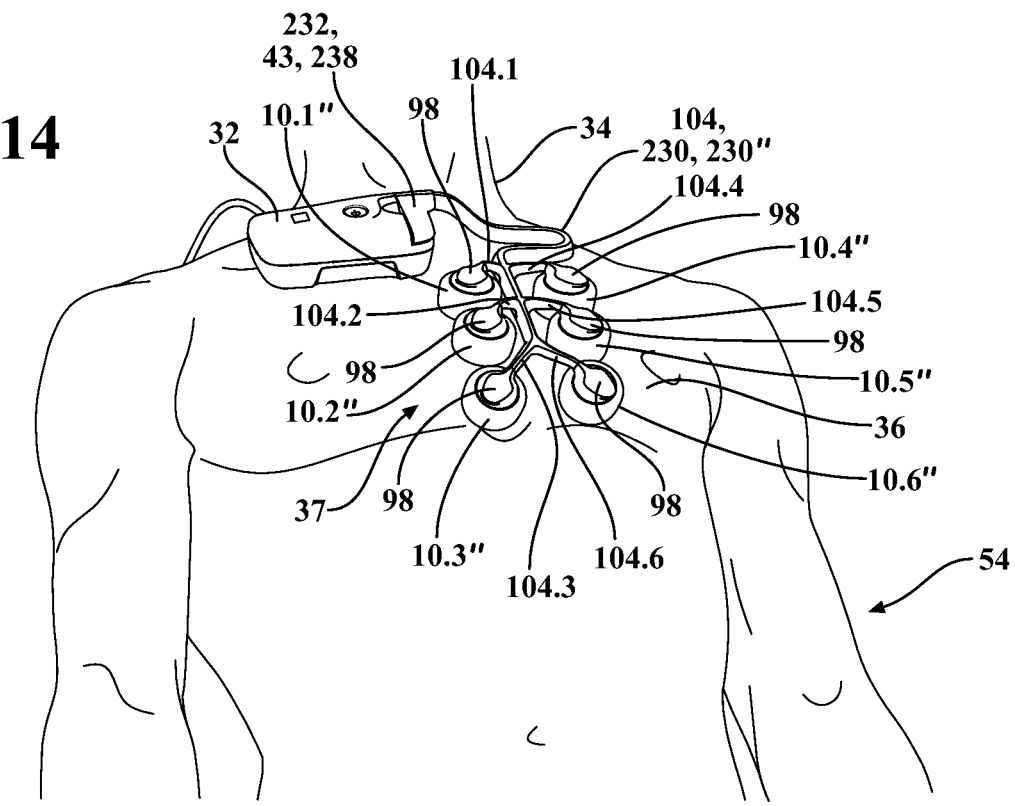
FIG. 14 illustrates the interconnection of a recording module to the plurality of second-aspect auscultatory sound-or-vibration sensors illustrated in FIG. 13 attached to the thorax of the test subject.
Figure 15:
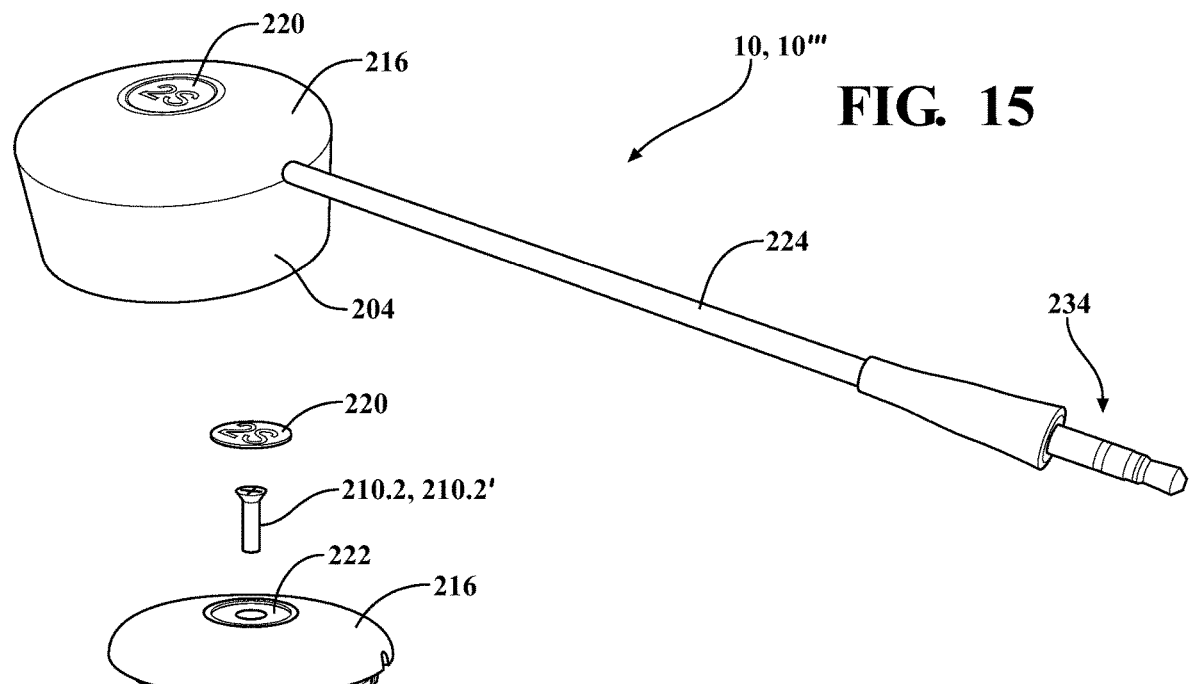
FIG. 15 illustrates an isometric view of an assembled third-aspect auscultatory sound-or-vibration sensor.

Referring to FIG. 12a, the second-aspect auscultatory sound-or-vibration sensors 10, 10" are utilized to gather auscultatory sound or vibration signals and ECG signals from a test subject 34 by first installing hydrogel pads 55, 56' on each of six auscultatory sound-or-vibration sensors 10.1", 10.2", 10.3", 10.4", 10.5", 10.6" to be used to gather the auscultatory sound or vibration signals at, for example, the third $44^{3L}$, $44^{3R}$, fourth $44^{4L}$, $44^{4R}$ and fifth $44^{5L}$, $44^{5R}$, intercostal spaces on the left and right sides of the test subject 34, respectively, wherein each hydrogel pad 55, 56' is installed on the respective auscultatory sound-or-vibration sensor 10.1", 10.2", 10.3", 10.4", 10.5", 10.6" after first removing one of the two opposing liners from the side of the hydrogel pad 55, 56' to be attached thereto. Then, continuing with the example, referring to FIGS. 12b and 13, the remaining liner 103 is removed from the hydrogel pad 55, 56' on the auscultatory sound-or-vibration sensor 10.5" to be installed at the fourth left intercostal space $44^{4L}$, and that auscultatory sound-or-vibration sensor 10.5" is installed at that location. Then, using the fourth left intercostal space $44^{4L}$ as a reference, the remaining auscultatory sound-or-vibration sensors 10" are similarly prepared and similarly installed at the remaining third $44^{3L}$, $44^{3R}$, fourth $44^{4R}$ and fifth $44^{5L}$, $44^{5R}$, intercostal spaces, using the best placement that is possible for each auscultatory sound-or-vibration sensor 10". Then, referring to FIG. 14, each of a plurality of second electrical connectors 98, each at the end of a corresponding branch 104.1, 104.2, 104.3, 104.4, 104.5, 104.6 of an associated tree-shaped wiring harness 104, is connected a corresponding auscultatory sound-or-vibration sensor 10.1", 10.2", 10.3", 10.4", 10.5", 10.6", in accordance with the inherent corresponding orientation of the associated branches 104.1, 104.2, 104.3, 104.4, 104.5, 104.6, each of which is operatively coupled to the electrical connector 43 that connects to the recording module 32. The ECG electrodes 74' of two of the auscultatory sound-or-vibration sensor 10.1", 10.2", 10.3", 10.4", 10.5", 10.6", for example, first 10.1" and sixth 10.6" auscultatory sound-or-vibration sensors, are used to provide the associated ECG signal. In one set of embodiments, an EGC body ground is provided by a conductive pad underneath the recording module 32, which is in contact with the skin 36 of the test subject 34 when the recording module 32 is connected to the electrical connector 43 of the first 42.1 and second 42.2 sensor assemblies and placed on the torso 54 of the test subject 34. Alternatively, one of the remaining auscultatory sound-or-vibration sensors 10.2", 10.3", 10.4", 10.5", for example, the third auscultatory sound-or-vibration sensor 10.3", may be used to define the ECG body ground for the recording module 32. In one set of embodiments, the selection of which of the auscultatory sound-or-vibration sensors 10.1", 10.2", 10.3", 10.4", 10.5", 10.6" are used as the ECG electrodes 74' and the ECG body ground electrode 74" is built into the tree-shaped wiring harness 104, the latter of which may be overmolded as described more fully hereinbelow.

Referring to FIGS. 15-17b, a third aspect 10' of an auscultatory sound-or-vibration sensor 10, 10''' is adapted to be relatively lighter and stiffer than the above-described first-aspect auscultatory sound-or-vibration sensor 10, 10', and is adapted with the plastic-film layer 46 being adhesively bonded to the metallic diaphragm disk substrate 22, so as to provide for a relatively higher resonant frequency and a relatively more direct coupling of the metallic diaphragm disk substrate 22 to the skin 36 of the test subject 34, resulting also in a relatively higher sensitivity. The third aspect 10''' auscultatory sound-or-vibration sensor 10, 10''' is also adapted to be relatively more mechanically isolated from other of a plurality of auscultatory sound-or-vibration sensors 10, 10''' when used collectively in a group, so as to reduce mechanical interference therebetween.

More particularly,—similar to the above-described first-aspect auscultatory sound-or-vibration sensor 10, 10'—the third-aspect auscultatory sound-or-vibration sensor 10, 10''' incorporates a piezoelectric sensor disk 12 that is adhesively bonded to a base rim 14' of a relatively shallow counterbore 16' in the open end 18.1' of a hollow inner housing 18', so as to close the open-ended hollow inner housing 18', thereby forming a cavity 20' therewithin. For example, in one set of embodiments, the hollow inner housing 18' is 3-D printed from polylactic acid (PLA), but alternatively could be made of any rigid plastic, for example, acrylic, acrylonitrile butadiene styrene (ABS) or Delrin®, for example by 3-D printing, injection molding or machining; or could be made from metal, for example, aluminum, brass, steel that is machined or cast, or a powdered metal composition that could be either sintered or additively manufactured.

The piezoelectric sensor disk 12—comprising a metallic diaphragm disk substrate 22 to which is bonded a layer of piezoelectric material 24 within a relatively central region 26 of the metallic diaphragm disk substrate 22 on the surface 22.1 of the metallic diaphragm disk substrate 22 facing the cavity 20', leaving an outer annular region 28 of the metallic diaphragm disk substrate 22 exposed—substantially the same as for the above-described first-aspect auscultatory sound-or-vibration sensor 10, 10'. Further similar to the above-described first-aspect auscultatory sound-or-vibration sensor 10, 10', the outer edge portion 22.1' of the cavity-facing surface 22.1 of the metallic diaphragm disk substrate 22 is adhesively bonded to the base rim 14' of the counterbore 16' in the open end 18.1' of the hollow inner housing 18' with a flexible adhesive 33 that provides for a flexible connection therebetween that readily accommodates sound-or-vibration-induced vibration of the metallic diaphragm disk substrate 22 without degradation of the associated adhesive bond, which effectively provides for the metallic diaphragm disk substrate 22 to "float" relative to the hollow inner housing 18'.

The hollow inner housing 18' is inserted within a first bore 202 in a first end 204.1 of a sleeve outer housing 204 incorporating an internal flange 206 against which the closed end 18.2' of the hollow inner housing 18' abuts a first side 206.1 thereof, and is keyed thereto by an associated key portion 207' of the internal flange 206 in cooperation with a keyway portion 207" of the hollow inner housing 18'.

As for the above-described first-aspect auscultatory sound-or-vibration sensor 10, 10', the third-aspect auscultatory sound-or-vibration sensor 10, 10''' further incorporates one or more inertial masses 35, 35.1, 35.2, but which are inserted within a second bore 208 in the second end 204.2 of the sleeve outer housing 204, and which abut a second side 206.2 of the internal flange 206. The hollow inner housing 18' and the inertial masses 35, 35.1, 35.2 are secured to one another and clamped across the internal flange 206, with a first machine screw 210.1—for example, a flat-head machine screw 210.1'—that is inserted through the closed end 18.2' of the hollow inner housing 18', through a clearance hole 212 in the lower inertial mass(es) 35.2, and which is screwed into a threaded hole 214 in the uppermost 35.1 (or sole) inertial mass 35. The second end 204.2 of the sleeve outer housing 204 is closed with a circular lid 216 that engages with, and is bonded to,—for example, using a cyano-acrylate glue,—a counterbore 218 in the second end 204.2 of the sleeve outer housing 204, and that is secured thereto with a second machine screw 210.2—for example, a flat-head machine screw 210.2'—that engages with the threaded hole 214 in the uppermost 35.1 (or sole) inertial mass 35, wherein the head of the second machine screw 210.2, 210.2' is covered with an identification plate 220, for example, inserted in, and adhesively bonded to, a corresponding recessed portion 222 in the center of the circular lid 216.

Figure 16:
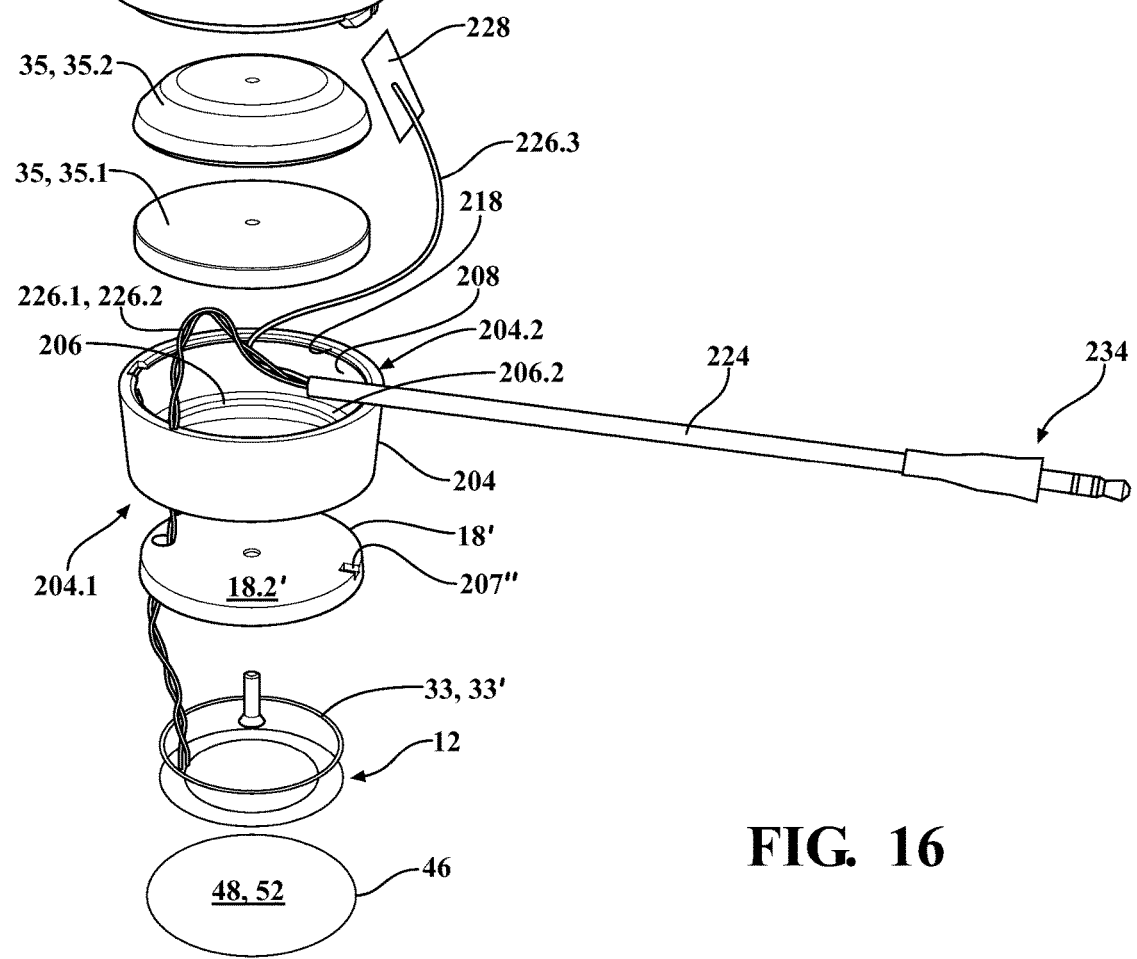
FIG. 16 illustrates an isometric exploded view of the third-aspect auscultatory sound-or-vibration sensor illustrated in FIG. 15.
Figure 17A:
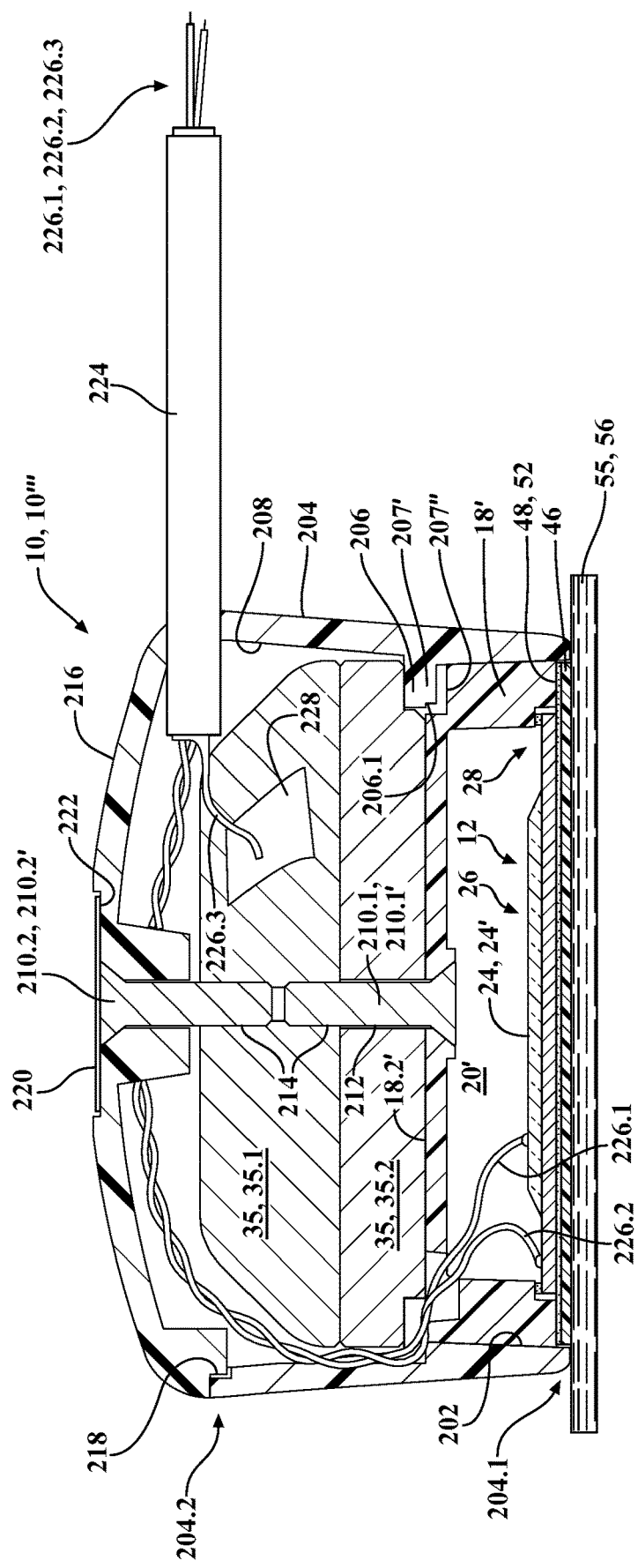
FIG. 17a illustrates a cross-sectional view of the third-aspect auscultatory sound-or-vibration sensor illustrated in FIGS. 15 and 16.
Figure 17B:
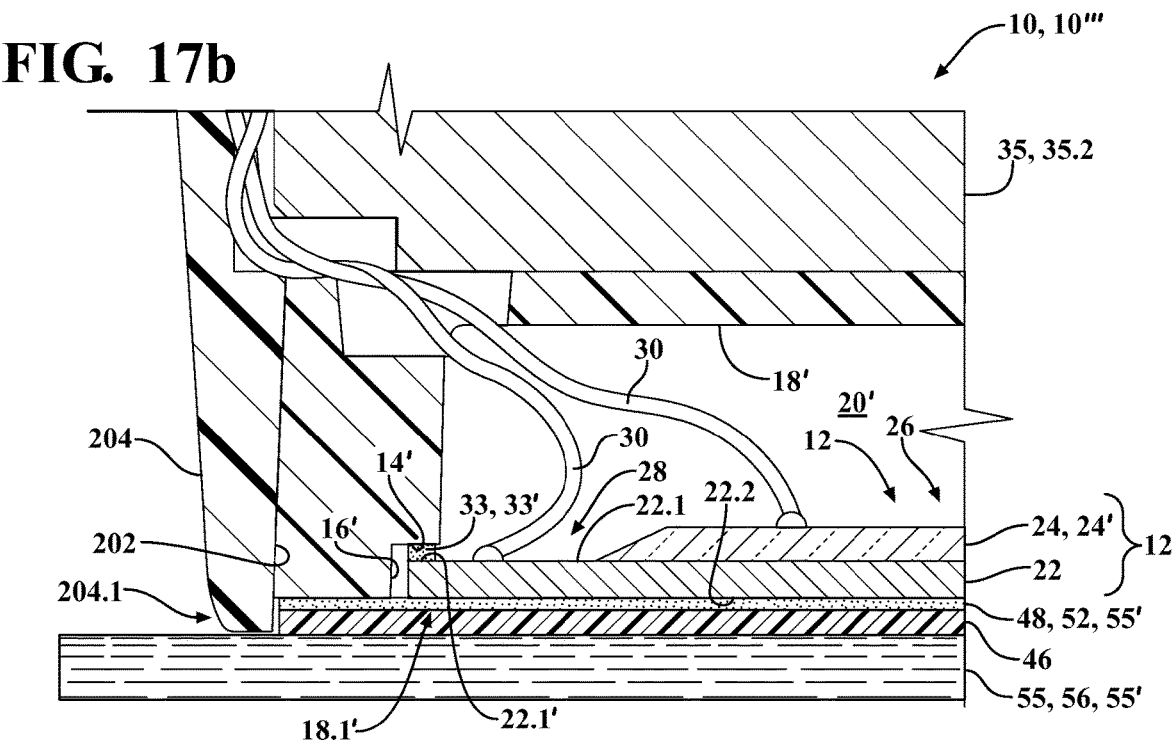
Figure 18:
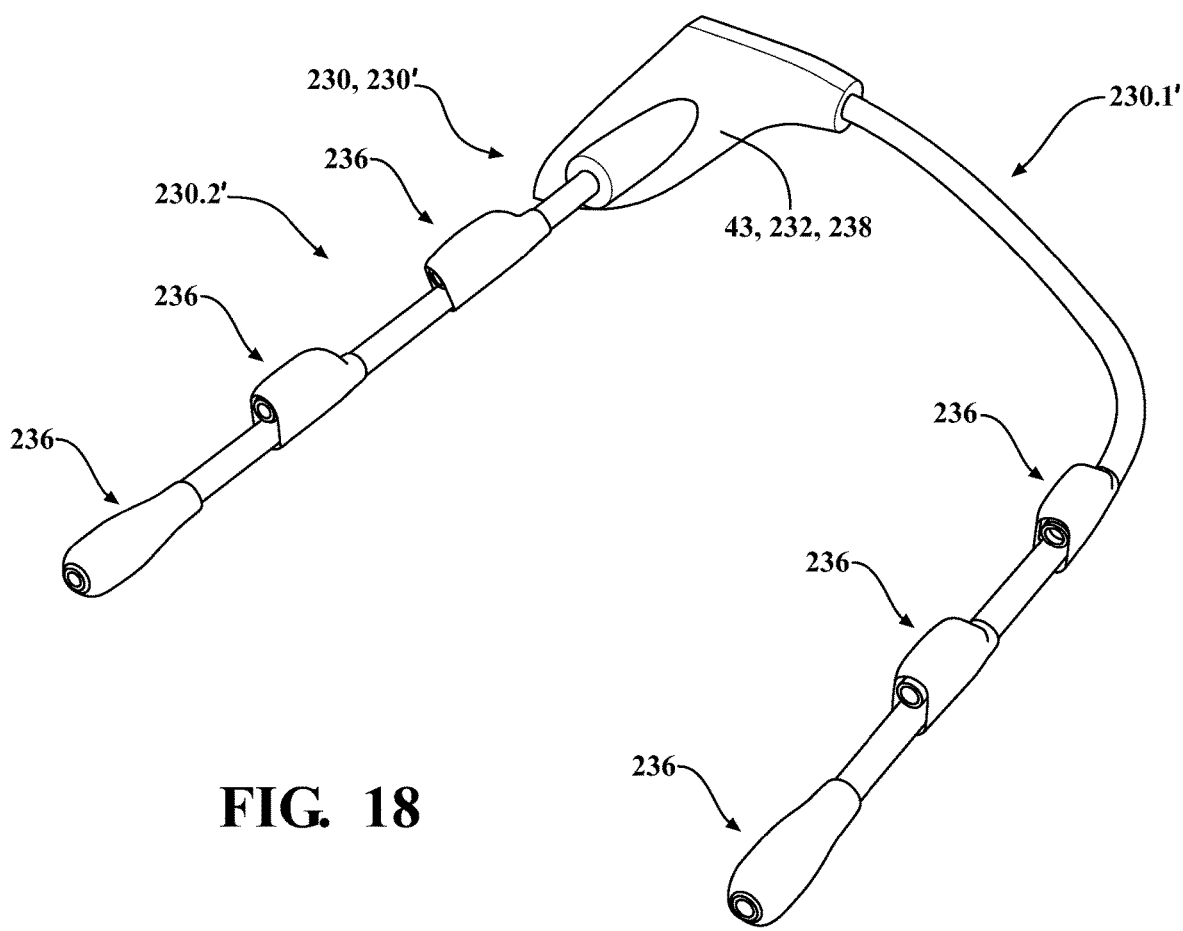
FIG. 18 illustrates a first aspect of a wiring harness that provides for operatively coupling a plurality of auscultatory sound-or-vibration sensors to an associated recording module, with the associated auscultatory sound-or-vibration sensors disconnected from the first-aspect wiring harness.

Referring to FIGS. 16 and 17, a plastic-film layer 46—for example, polyester or mylar, for example, in one set of embodiments, a 3 mil thick plastic-film layer 46—is adhesively bonded to the outwardly-facing surface 22.2 of the metallic diaphragm disk substrate 22 with a double-sided adhesive tape 48, for example, 3M® 468MP adhesive transfer tape comprising a 5 mil thick acrylic adhesive. The plastic-film layer 46 provides for receiving a hydrogel material 55, 56—or generally, a material providing for an acoustically-transmissible-adhesive interface 55 between the third aspect 10''' auscultatory sound-or-vibration sensor 10, 10''' and the skin 36 of the test subject 34,—which in cooperation with the double-sided adhesive tape 48 between the plastic-film layer 46 and the metallic diaphragm disk substrate 22, provides for an effective adhesive interface 55' between the skin 36 of the test subject 34 and the metallic diaphragm disk substrate 22 of the piezoelectric sensor disk 12, which acts both to retain the third aspect 10''' auscultatory sound-or-vibration sensor 10, 10''' on the skin 36 of a test subject 34 whose torso 54 is inclined, and to more effectively transmit auscultatory sounds or vibrations to the piezoelectric sensor disk 12. In cooperation with a relatively rigid third-aspect auscultatory sound-or-vibration sensor 10, 10''', the effective adhesive interface 55' between the skin 36 of the test subject 34 and the metallic diaphragm disk substrate 22 of the piezoelectric sensor disk 12 provides for coupling more of the vibrational energy induced by the inertial masses 35, 35.1, 35.2 into the piezoelectric material 24, 24', 24" where it is transduced into an associated resulting electrical voltage, and provides for enhancing the associated low-frequency sensitivity and reducing the variance of the associated frequency response in the corresponding range of frequencies.

The third-aspect auscultatory sound-or-vibration sensor 10, 10''' incorporates an integral electrical lead 224 that provides for electrically coupling the third aspect 10''' auscultatory sound-or-vibration sensor 10, 10''' to the recording module 32, with respective associated conductive leads 226.1, 226.2, 226.3 respectively connected to the piezoelectric material 24 of the piezoelectric sensor disk 12, to the associated metallic diaphragm disk substrate 22; and to a ground tab 228 placed against the uppermost 35.1 (or sole) inertial mass 35 so as to provide associated electrical shielding. Accordingly, with each third-aspect auscultatory sound-or-vibration sensor 10, 10''' of an associated plurality of third-aspect auscultatory sound-or-vibration sensors 10, 10''' having an integral electrical lead 224 that does not directly mechanically connect to another of the plurality of third-aspect auscultatory sound-or-vibration sensors 10, 10''', the third-aspect auscultatory sound-or-vibration sensors 10, 10''' are relatively more mechanically isolated from one another—relative to the above-described interconnected first-aspect auscultatory sound-or-vibration sensor 10, 10'—which provides for relatively-improved fidelity of the associated auscultatory sound or vibration signals detected thereby.

Figure 19:
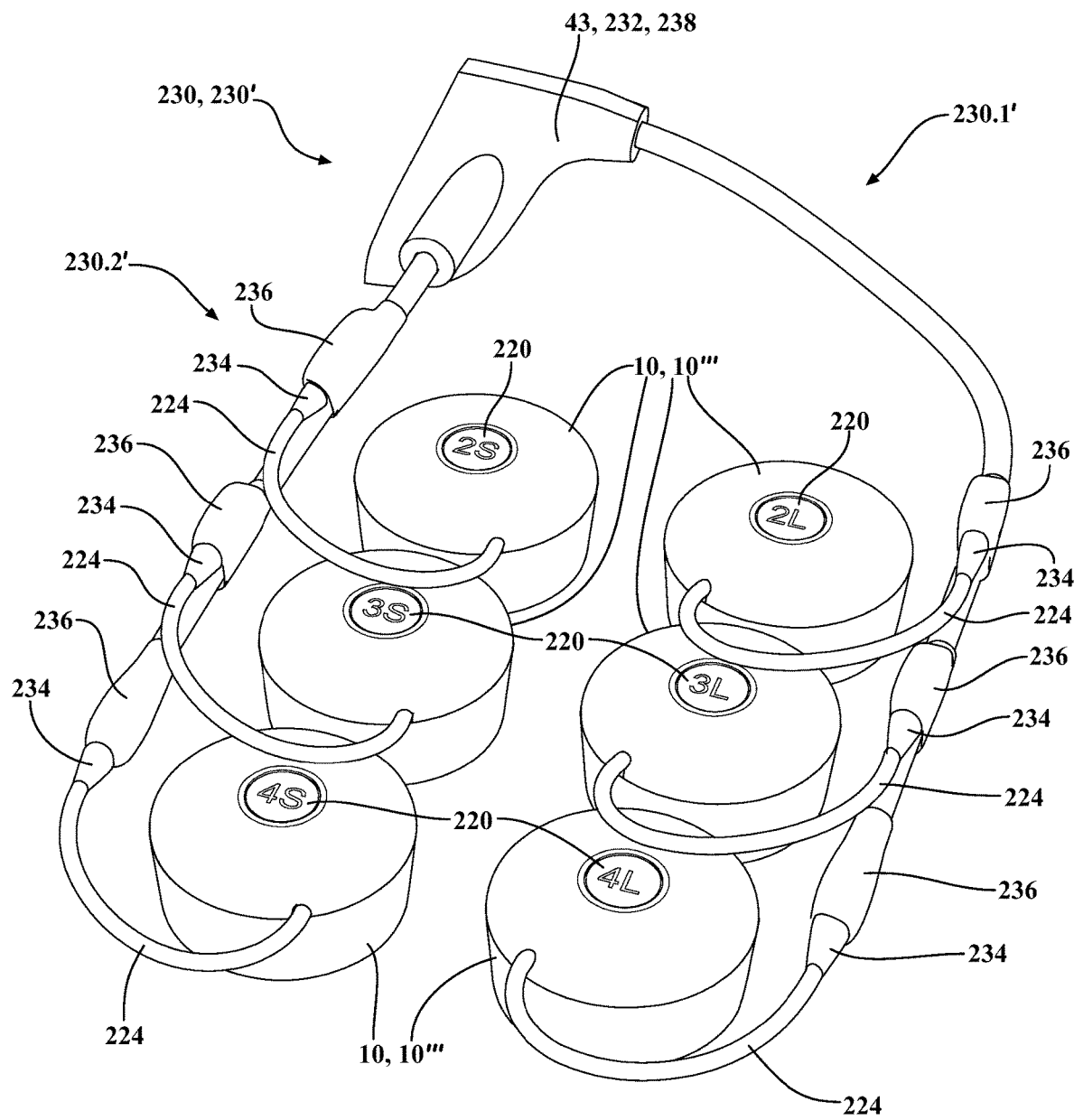
FIG. 19 illustrates the first-aspect wiring harness illustrated in FIG. 19, in cooperation with a plurality of six third-aspect auscultatory sound-or-vibration sensors connected thereto.
Figure 20A:
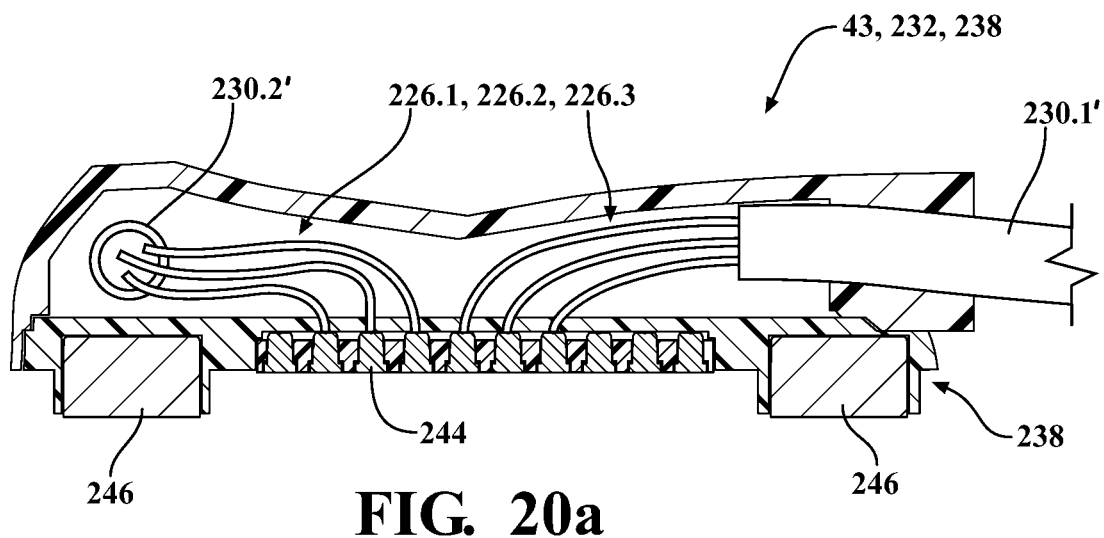
FIG. 20a illustrates a cross-sectional view of a connector portion of the wiring harness illustrated in FIGS. 18 and 19, and a corresponding mating connector of an associated recording module.
Figure 20B:
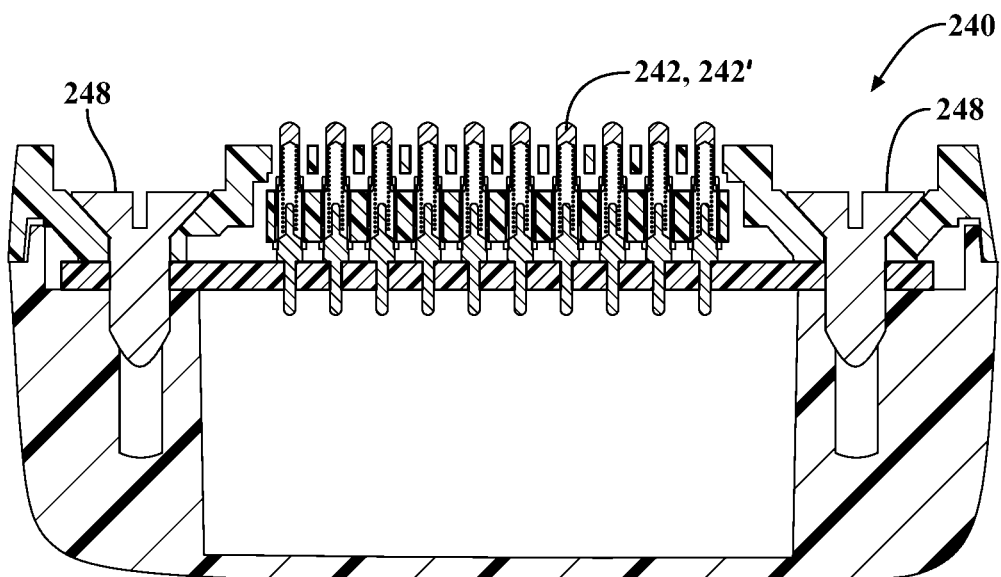
Figure 20C:
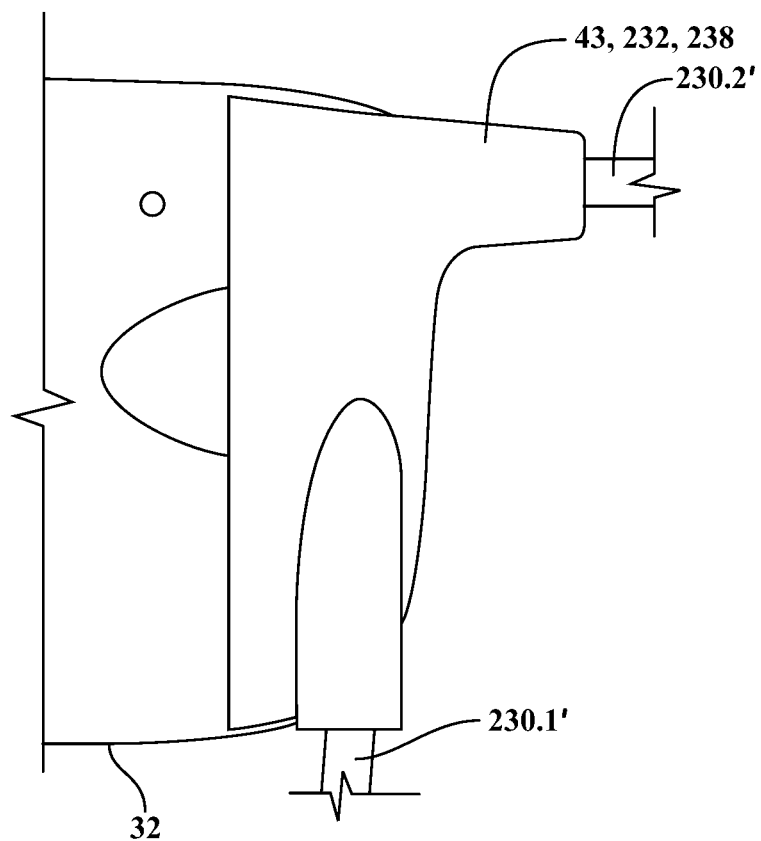
FIG. 20c illustrates a top view of an assembly of the two connector portions illustrated in FIGS. 20a and 20b, in cooperation with the recording module.
Figure 20D:
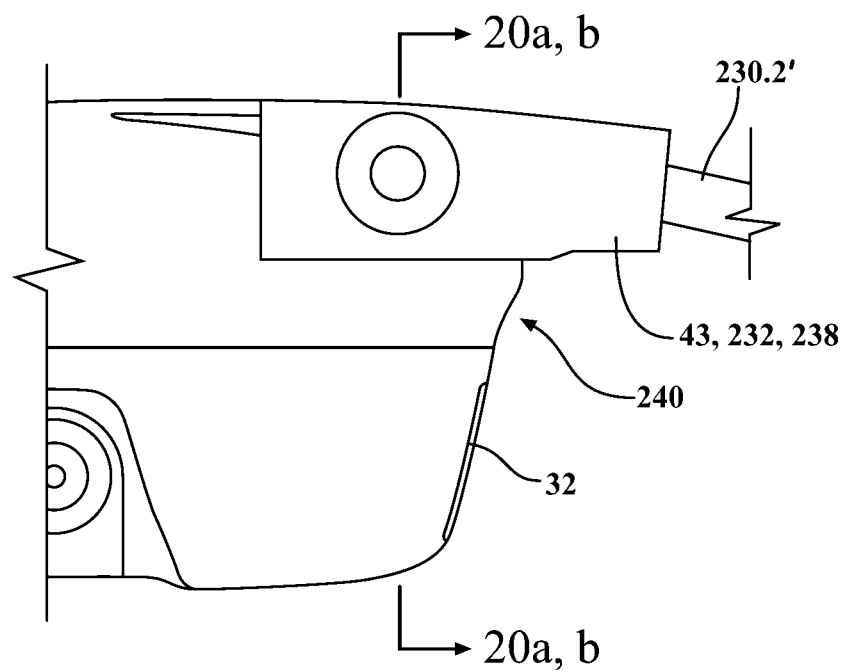
FIG. 20d illustrates a side view of an assembly of the two connector portions illustrated in FIGS. 20a and 20b, in cooperation with the recording module.

Referring to FIGS. 15, 16, 18 and 19, in accordance with one set of embodiments, a first aspect 230' of a wiring harness 230, 230' provides for a plurality of auscultatory sound-or-vibration sensors 10, 10', 10", 10''' to be electrically connected to an associated recording module 32 via an associated recording-module connector 232. More particularly, referring to FIGS. 15, 16 and 19, each of the individual electrical leads 224 from the associated auscultatory sound-or-vibration sensors 10, 10', 10", 10''' is terminated with a corresponding associated electrical plug connector 234 that is configured to engage with any one of a plurality of electrical jack connectors 236 incorporated in the wiring harness 230, 230', wherein the associated corresponding electrical contacts of each electrical jack connector 236 are electrically connected to corresponding contacts of the recording-module connector 232 via corresponding conductors within the wiring harness 230, 230', and each of the electrical jack connectors 236 are located along the wiring harness 230, 230' so as to inherently suggest—by its location—with a corresponding location on the thorax 37 of the test subject 34. For example, in the embodiment illustrated in FIGS. 18 and 19, the wiring harness 230, 230' is bifurcated into first 230.1' and second 230.2' branches, each branch 230.1', 230.2' incorporating three electrical jack connectors 236 that provide accommodating auscultatory sound-or-vibration sensors 10, 10', 10", 10''' associated with a corresponding associated common lateral location, for example, right R, sternum S or Left L associated with a corresponding set of inter-costal spaces. The particular locations of the auscultatory sound-or-vibration sensors 10, 10', 10", 10''' may also be identified by corresponding indicia on an identification plate 220 associated with each auscultatory sound-or-vibration sensor 10, 10', 10", 10''. For example, FIG. 19 illustrates a plurality of six third-aspect auscultatory sound-or-vibration sensors 10, 10''', each incorporating a corresponding integral electrical lead 224 that is terminated with a corresponding associated electrical plug connector 234, wherein each electrical plug connector 234 is connected to a corresponding electrical jack connector 236 of the wiring harness 230, 230', and each of the third-aspect auscultatory sound-or-vibration sensors 10, 10''' is identified—by the indicia on its corresponding identification plate 220—with the corresponding location on the thorax 37 of the test subject 34, for example, the following correspondence between indicia and corresponding associated inter-costal space: 2S=$2^{nd}$ sternum/central inter-costal space; 3S=$3^{rd}$ sternum/central inter-costal space; 4S=$4^{th}$ sternum/central inter-costal space; 2L=$2^{nd}$ left inter-costal space; 3L=$3^{rd}$ left inter-costal space; 4L=$4^{th}$ left inter-costal space.

Referring to FIG. 20, in accordance with one set of embodiments, the wiring harness 230, 230' is terminated with a magnetically-attachable multi-conductor connector 238 that is adapted to engage with a corresponding multi-terminal mating connector 240 of the recording module 32, wherein one of the multi-terminal mating connector 240 and the magnetically-attached multi-conductor connector 238 incorporates a plurality of spring-loaded conductive pins 242, for example, Pogo-pins 242', and the other of the magnetically-attached multi-conductor connector 238 and the multi-terminal mating connector 240 incorporates a corresponding plurality of conductive terminals 244, wherein each of the spring-loaded conductive pins 242, 242' or conductive terminals 244 of the magnetically-attachable multi-conductor connector 238 is electrically coupled to a corresponding conductive lead 226.1, 226.2, 226.3 of the wiring harness 230, 230'. Each of the spring-loaded pins 242, 242' contacts a corresponding conductive terminal 244 when the magnetically-attachable multi-conductor connector 238 of the wiring harness 230, 230' is engaged with to the corresponding multi-terminal mating connector 240 of the recording module 32, wherein the engagement of the magnetically-attachable multi-conductor connector 238 with the multi-terminal mating connector 240 when attached thereto is maintained by a plurality of magnets 246 associated with one of the magnetically-attachable multi-conductor connector 238 and the multi-terminal mating connector 240, for example, associated with the magnetically-attachable multi-conductor connector 238; that magnetically engage with a corresponding plurality of ferromagnetic mounting screws 248 associated with the other of the multi-terminal mating connector 240 and the magnetically-attachable multi-conductor connector 238, for example, associated with the multi-terminal mating connector 240, that secure the multi-terminal mating connector 240 to the recording module 32.

Referring to FIGS. 21 and 22a-22c, in accordance with a second aspect 230'' of a wiring harness 230, 230'', the individual conductive leads 226.1, 226.2, 226.3 from each auscultatory sound-or-vibration sensor 10, 10', 10'', 10', or from an associated second electrical connector 98 associated with a second-aspect auscultatory sound-or-vibration sensor 10, 10'', to the associated electrical connector 43, 232, 238 that provides for releasably coupling to a mating connector 240 of the recording module 32, for each of a plurality of auscultatory sound-or-vibration sensor 10, 10', 10'', 10''', thereby providing for operatively coupling each of the plurality of auscultatory sound-or-vibration sensors 10, 10.1', 10.2', 10.3' to the recording module 32. Each of the sets of conductive leads 226.1, 226.2, 226.3 associated with each of the auscultatory sound-or-vibration sensor 10, 10', 10'', 10' is overmolded with a relatively-low-durometer elastomeric sheath 250—for example, having a durometer in the range of Shore 00-10 to 00-50—that is continuous between each auscultatory sound-or-vibration sensor 10, 10.1', 10.2', 10.3' and the electrical connector 43. The second-aspect wiring harness 230, 230'' incorporates a central spine portion 252, with a plurality of branch portions 254 extending therefrom, each of which operatively couples a corresponding auscultatory sound-or-vibration sensor 10, 10.1', 10.2', 10.3' to the central spine portion 252.

Figure 21:
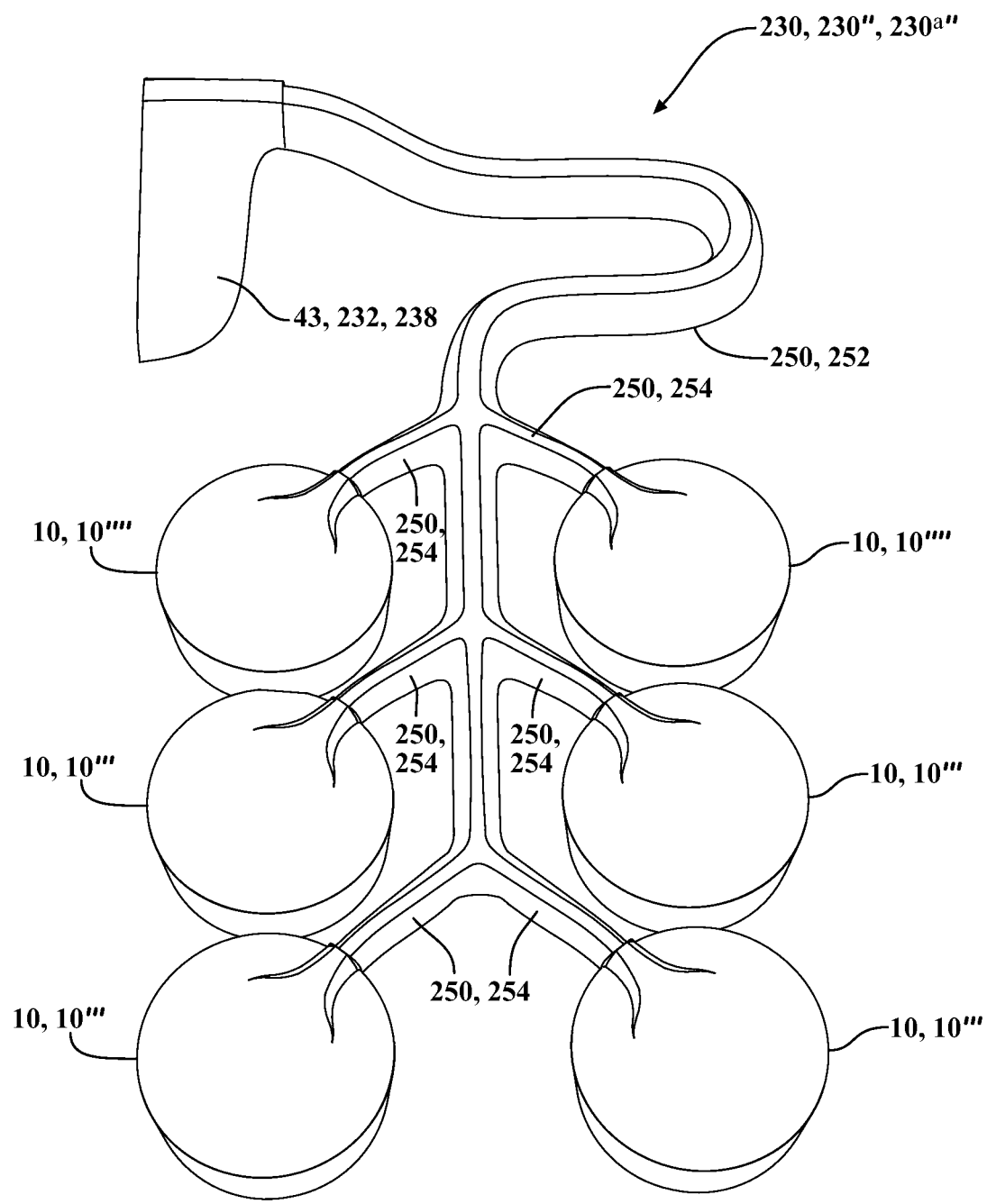
FIG. 21 illustrates a first embodiment of a second aspect of a wiring harness that provides for operatively coupling a plurality of auscultatory sound-or-vibration sensors to an associated recording module, illustrated in cooperation with a plurality of third-aspect auscultatory sound-or-vibration sensors.
Figure 22B:
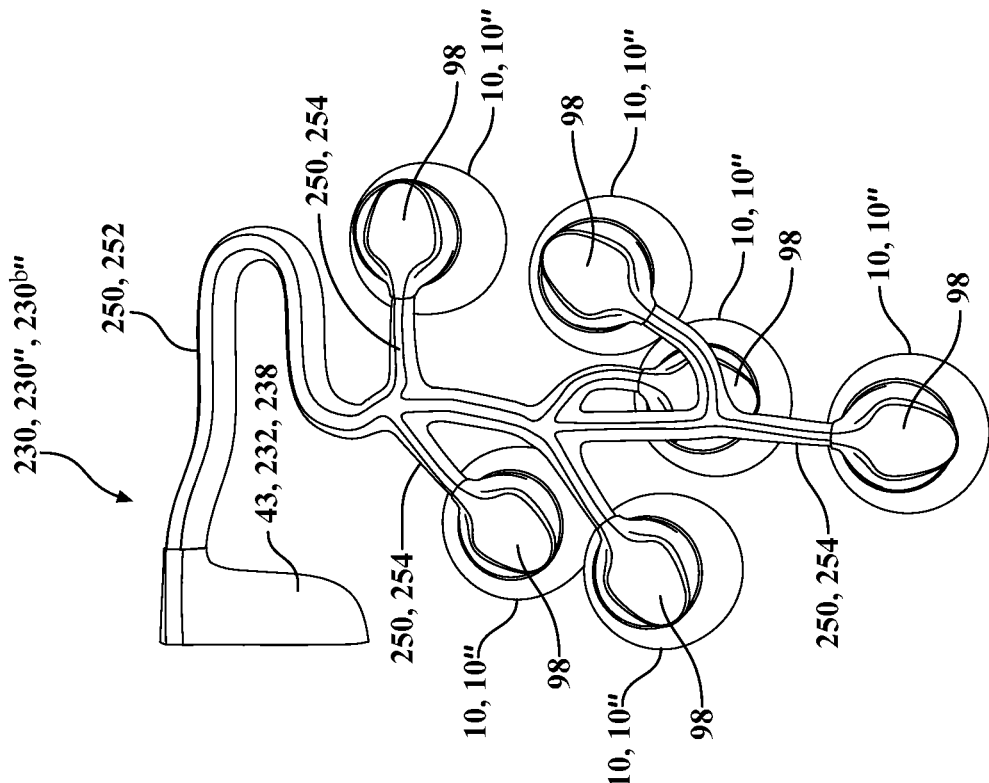
FIG. 22b illustrates the second embodiment of the second-aspect wiring harness illustrated in FIG. 22a that provides for operatively coupling a plurality of auscultatory sound-or-vibration sensors to an associated recording module, but illustrated in cooperation with a plurality of second-aspect auscultatory sound-or-vibration sensors in a second orientation relative to one another.
Figure 22A:
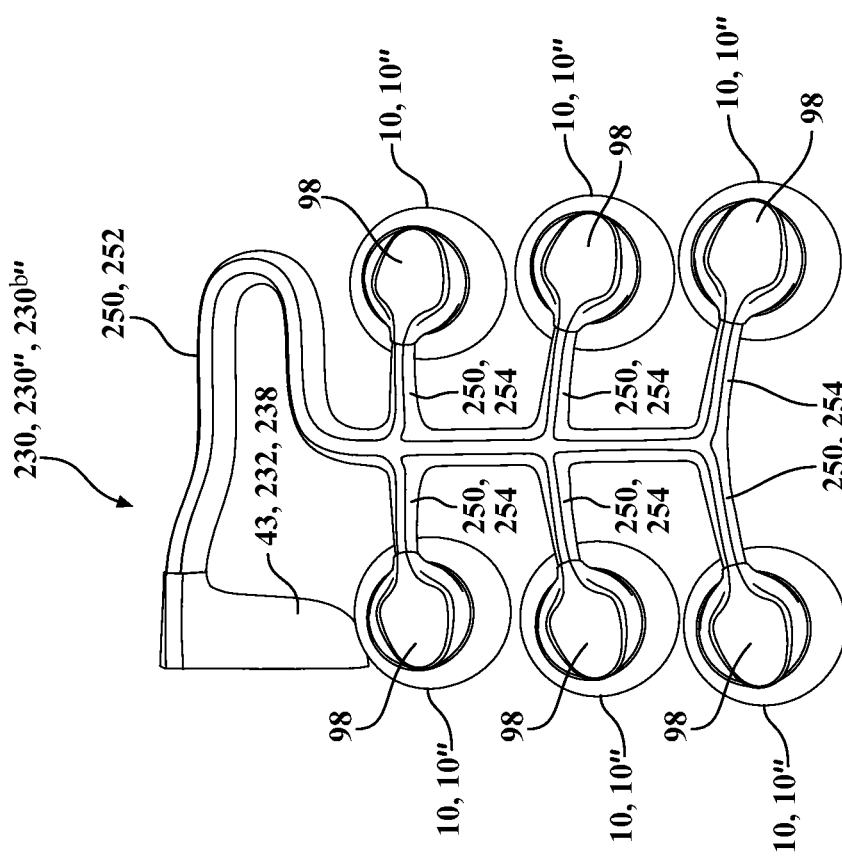
FIG. 22a illustrates a second embodiment of the second-aspect wiring harness that provides for operatively coupling a plurality of auscultatory sound-or-vibration sensors to an associated recording module, illustrated in cooperation with a plurality of second-aspect auscultatory sound-or-vibration sensors in a first orientation relative to one another.
Figure 22C:
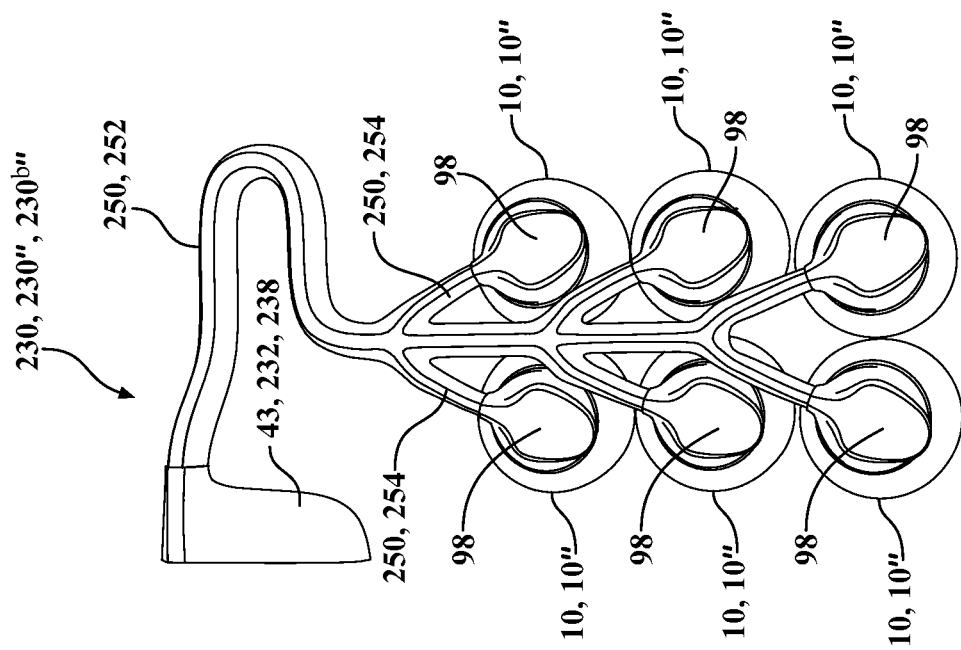
FIG. 22c illustrates the second embodiment of the second-aspect wiring harness illustrated in FIGS. 22a and 22b that provides for operatively coupling a plurality of auscultatory sound-or-vibration sensors to an associated recording module, but illustrated in cooperation with a plurality of second-aspect auscultatory sound-or-vibration sensors in a third orientation relative to one another.

Referring to FIG. 21, in accordance with a first embodiment, the second-aspect wiring harness 230, $230^{a}$'' that operatively couples a plurality of six third-aspect auscultatory sound-or-vibration sensors 10, 10''' to the associated electrical connector 43, the latter of which provides for operatively coupling to the recording module 32. Referring to FIGS. 22a-22c, in accordance with a second embodiment, the second-aspect wiring harness 230, $230^{b}$'' operatively couples a plurality of six second electrical connectors 98—each of which is associated with a corresponding second-aspect auscultatory sound-or-vibration sensor 10, 10'' so as to provide for being removably coupled thereto,— so as to provide for operatively coupling a corresponding plurality of six second-aspect auscultatory sound-or-vibration sensors 10, 10'' to the electrical connector 43, 232, 238 that couples to the recording module 32, when the second electrical connectors 98 are each connected to the corresponding second-aspect auscultatory sound-or-vibration sensors 10, 10''. The relatively-low-durometer elastomeric sheath 238 provides for a relatively flexible associated central spine portion 240, and associated plurality of branch portions 24 of the second-aspect wiring harness 230, 230'', $230^{a}$''', $230^{b}$'', which provides for readily positioning the associated auscultatory sound-or-vibration sensors 10, 10.1', 10.2', 10.3' to whichever locations are necessary for a particular test, so as to provide for readily adapting to the physical attributes of a particular test subject 34. For example, FIG. 22a illustrates the associated second-aspect auscultatory sound-or-vibration sensors 10, 10'' maximally laterally separated from one another. Furthermore, FIG. 22b illustrates the associated second-aspect auscultatory sound-or-vibration sensors 10, 10'' arranged with a cluster of four of the second-aspect auscultatory sound-or-vibration sensors 10, 10'' relatively-closely-spaced, and two of the second-aspect auscultatory sound-or-vibration sensors 10, 10'' spaced apart from one another, and from the cluster of four intermediate second-aspect auscultatory sound-or-vibration sensors 10, 10''. Yet further, FIG. 22c illustrates the associated second-aspect auscultatory sound-or-vibration sensors 10, 10'' positioned relatively closely to one another.

Figure 23:
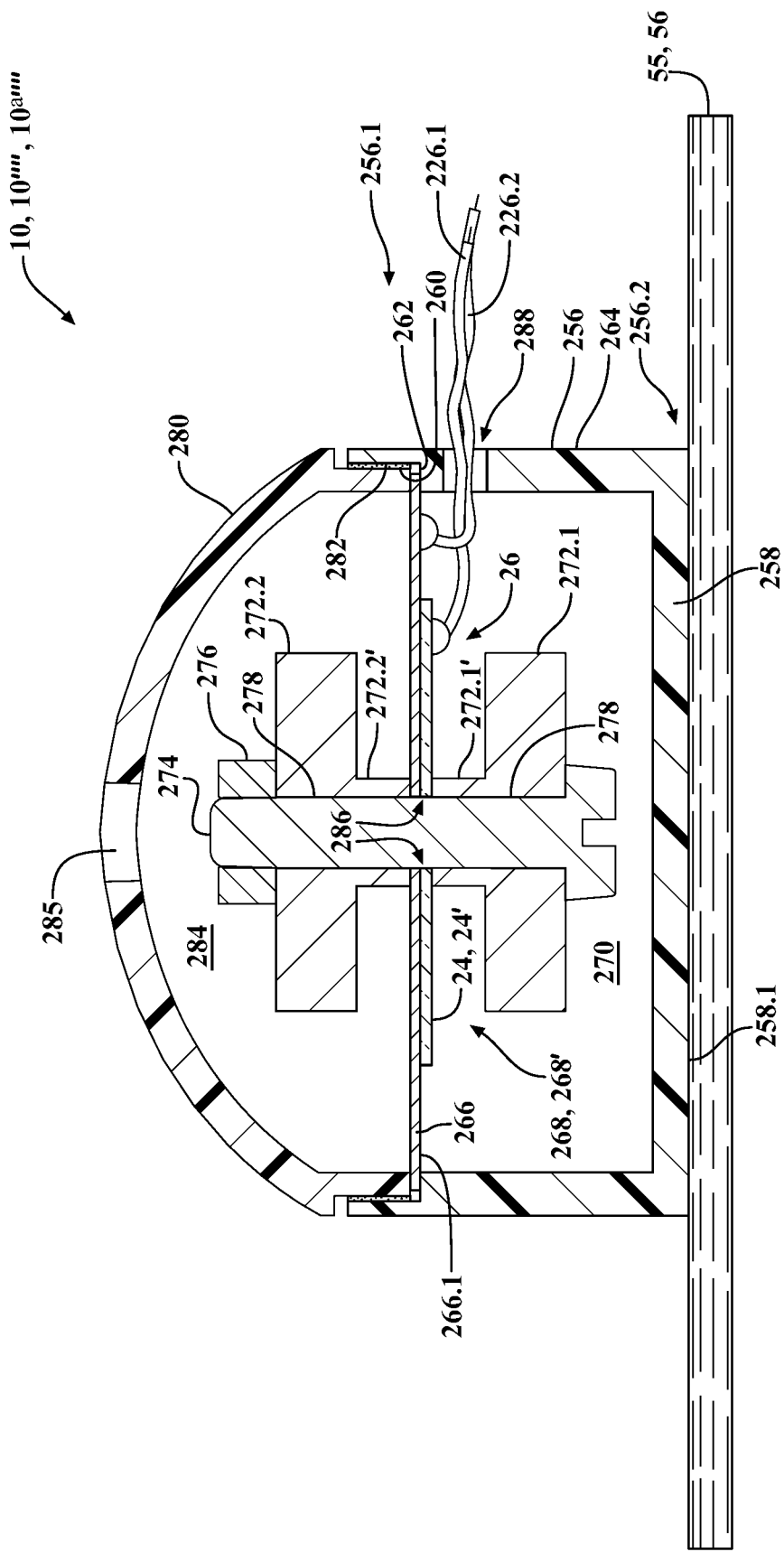
FIG. 23 illustrates a cross-sectional view of a first embodiment of a fourth-aspect of an auscultatory sound-or-vibration sensor incorporating a first-aspect piezoelectric sensor disk.
Figure 24:
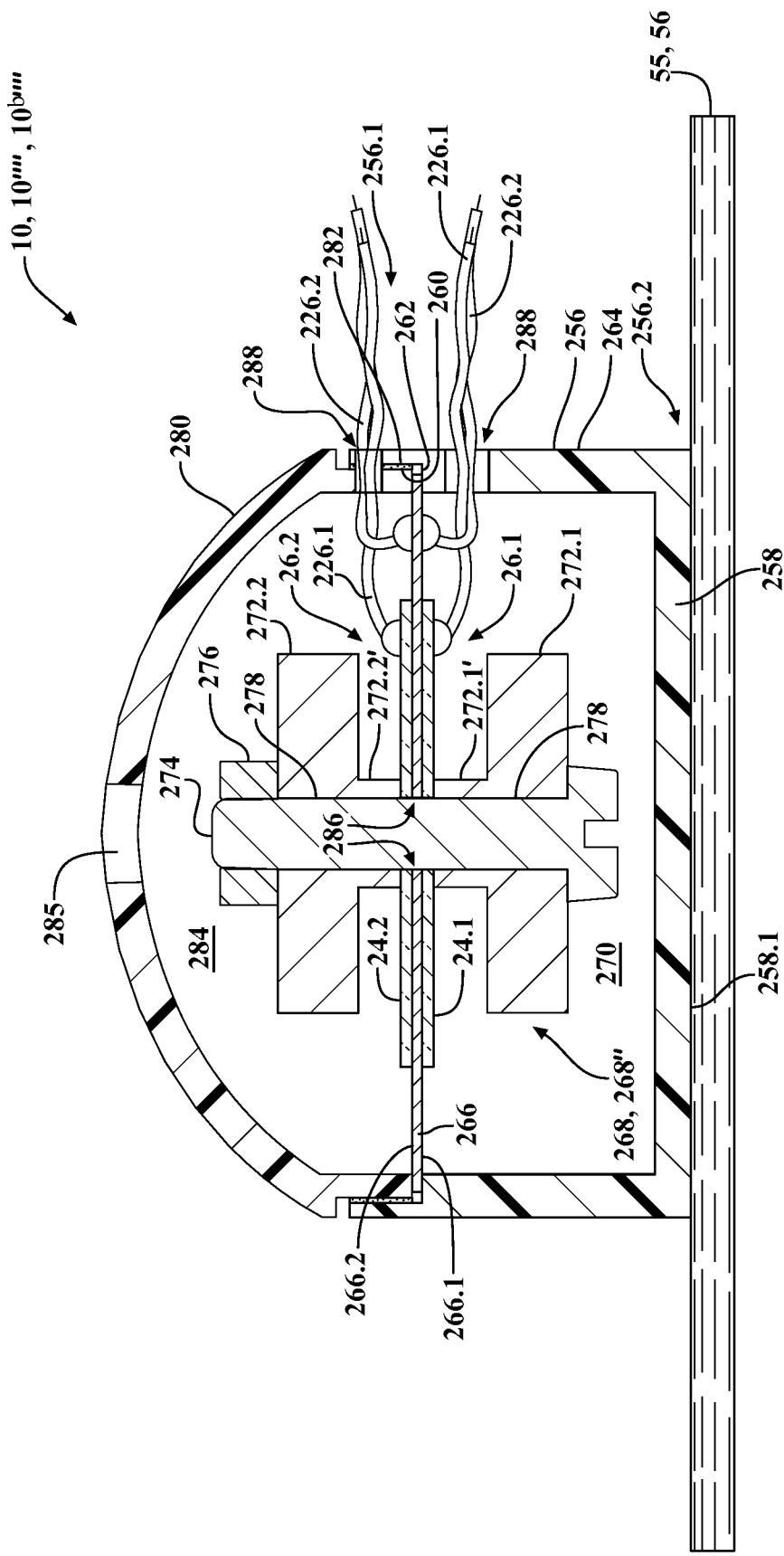
FIG. 24 illustrates a cross-sectional view of a second embodiment of the fourth-aspect auscultatory sound-or-vibration sensor incorporating a second-aspect piezoelectric sensor disk.
Figure 25:
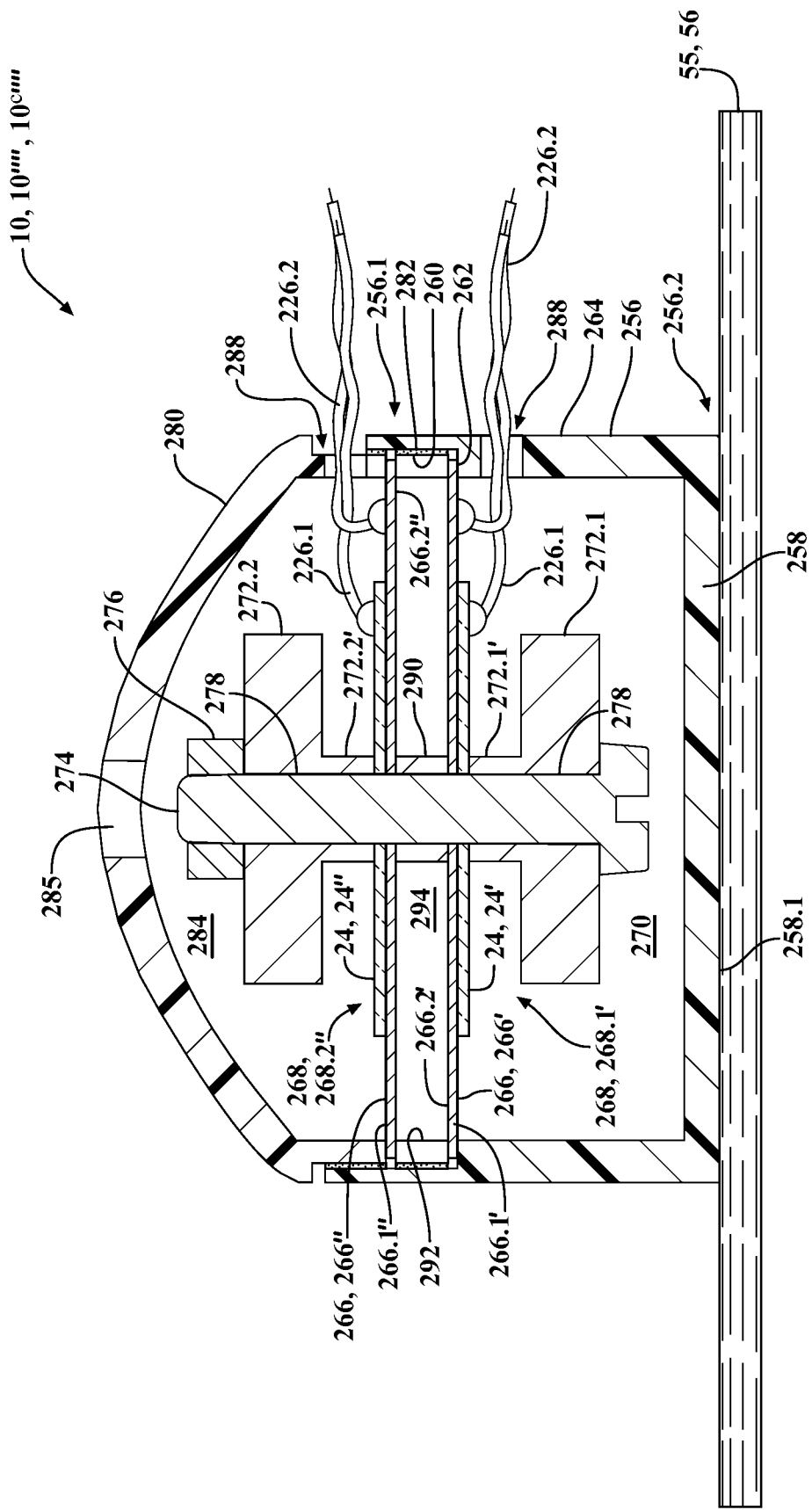
FIG. 25 illustrates a cross-sectional view of a third embodiment of the fourth-aspect auscultatory sound-or-vibration sensor incorporating a plurality of first-aspect piezoelectric sensor disks.

Referring to FIGS. 23-25, in accordance with a fourth aspect 10'''', the auscultatory sound-or-vibration sensor 10, 10'''' comprises an open-ended hollow housing 256 having and open 256.1 and closed 256.2 ends. The closed end 256.2 of the hollow housing 256 constitutes a flat base 258, the outer surface 258.1 of which provides for accepting an associated acoustically-transmissible-adhesive interface 55, for example, an associated hydrogel material 56, 55, that provides for attaching the auscultatory sound-or-vibration sensor 10, 10'''' to the skin 36 of the test subject 34. The open end 256.1 of the hollow housing 256 incorporates a counterbore 260, the base of which defines a base rim 262 within the sidewall 264 of the hollow housing 256, upon which is located a metallic diaphragm disk substrate 266 of an associated piezoelectric sensor disk 268, which closes a first portion of the hollow housing 256, so as to define an associated first, lower cavity 270 therewithin. A pair of first 272.1 and second 272.2 necked mass elements—also referred to as inertial masses—are clamped across the center of to the piezoelectric sensor disk 268 by a non-conductive screw 274, either in cooperation with an associated nut 276 with the non-conductive screw 274 extending through corresponding clearance holes 278 in both the first 272.1 and second 272.2 necked mass elements,—or alternatively, screwed into an internally-threaded portion of one of the first 272.1 and second 272.2 necked mass elements with the other of the first 272.1 and second 272.2 necked mass elements incorporating the associated clearance hole 278,—with the corresponding associated neck portions 272.1', 272.2'—also referred to as stand-off elements—of the first 272.1 and second 272.2 necked mass elements facing one another and abutting the piezoelectric sensor disk 268 so as to reduce the contact area therebetween. Generally, the stand-off elements may be either integral with the associated inertial mass elements, or distinct therefrom. The stand-off element has a reduced transverse dimension relative to a maximum transverse dimension of the associated inertial mass element, wherein the transverse dimension is relative to a direction that is generally parallel to a surface of the associated metallic diaphragm disk substrate 266. The transverse extent of the stand-off element(s) is reduced relative to that of the associated inertial mass so as to limit the otherwise stiffening effect of the stand-off element on the stiffness and associated resonant frequency of the metallic diaphragm disk substrate 266. For example, in one set of embodiments, a ratio of the transverse dimension of the stand-off element to the maximum transverse dimension of the metallic diaphragm disk substrate 266 is less than 0.2. The portion of the open-ended bore surface of the counterbore 260 extending beyond the piezoelectric sensor disk 268 is closed with a housing cap 280 that mates therewith and is bonded thereto, for example, with cyano-acrylate glue 282, so as to thereby define a second, upper cavity 284, wherein different first 272.1 and second 272.2 necked mass elements are located within corresponding different corresponding first 270 and second 284 cavities. As illustrated in FIGS. 23-25, depending upon the configuration, the fourth-aspect auscultatory sound-or-vibration sensor 10, 10"" incorporates either one or a plurality of piezoelectric sensor disks 268, of various configurations. In one set of embodiments, the second, upper cavity 284 is vented—for example, through a vent hole 285 in the housing cap 280 (also referred to as a cover), or alternatively or in combination, elsewhere through the housing,—for example, wherein the total vent area is sufficient so that the resonant frequency of the piezoelectric sensor disk 268 is substantially unaffected by the presence of the housing cap 280.

For example, referring to FIG. 23, a first embodiment 10, $10^{a\prime\prime\prime\prime}$ of the fourth-aspect auscultatory sound-or-vibration sensor 10, $10^{a\prime\prime\prime\prime}$ incorporates a single first aspect piezoelectric sensor disk 268' comprising a metallic diaphragm disk substrate 266 upon which—on a first side 266.1 thereof—is bonded a layer of piezoelectric material 24 within a relatively central region 26 thereof, further incorporating a central hole 286 through both the metallic diaphragm disk substrate 266 and the piezoelectric material 24 that accommodates the above-described non-conductive screw 274. The piezoelectric material 24 is located within an annular region centered about the central hole 286. The non-conductive screw 274 is non-conductive so as to prevent the bulk of the piezoelectric material 24 from being electrically shorted to the metallic diaphragm disk substrate 266 thereby. Alternatively, the non-conductive screw 274 could be replaced with a conductive screw if the inner diameter of the annular region of piezoelectric material 24 is sufficiently large so as to not contact either the neck portion 272.1' of the first necked mass element 272.1 adjacent thereto, or so as to not contact the conductive screw if the neck portion 272.1' of the first necked mass element 272.1 is either constructed of a non-conductive material or is electrically insulated from the piezoelectric material 24. A pair of conductive leads 226.1, 226.2 are respectively electrically connected to the piezoelectric material 24 and the metallic diaphragm disk substrate 266, respectively. The pair of conductive leads 226.1, 226.2 extends through a through-hole 288 in the sidewall 264 of the hollow housing 256, so as to provide for operatively coupling to, or incorporation in, an associated wiring harness 230, 230', 230" that provides for operatively coupling an electrical signal—responsive to a vibration-induced flexion of the metallic diaphragm disk substrate 266—from the piezoelectric sensor disk 268' to the recording module 32.

For another example, referring to FIG. 24, a second embodiment 10, $10^{b\prime\prime\prime\prime}$ of the fourth-aspect auscultatory sound-or-vibration sensor 10, $10^{b\prime\prime\prime\prime}$ incorporates a single, second aspect piezoelectric sensor disk 268"—also referred to as a bimorph—comprising a metallic diaphragm disk substrate 266 upon which are bonded two layers of piezoelectric material 24, 24.1, 24.2 on opposing sides 266.1, 266.2 of the metallic diaphragm disk substrate 266, within corresponding associated relatively central regions 26.1, 26.2 thereof, further incorporating a central hole 286 through both the metallic diaphragm disk substrate 266 and both layers piezoelectric material 24.1, 24.2 that accommodates the above-described non-conductive screw 274. For each layer of piezoelectric material 24.1, 24.2, the piezoelectric material 24 located within a corresponding annular region centered about the central hole 286. The non-conductive screw 274 is non-conductive so as to prevent the bulk of the piezoelectric material 24, 24.1, 24.2 of each layer from being electrically shorted to the metallic diaphragm disk substrate 266 thereby. Alternatively, similar to the above-described first embodiment 10, $10^{a\prime\prime\prime\prime}$, the non-conductive screw 274 could be replaced with a conductive screw if the inner diameter of the annular region of piezoelectric material 24 is sufficiently large so as to not contact either the neck portions 272.1', 272.2' of the corresponding the first 272.1 and second 272.2 necked mass elements adjacent thereto, or so as to not contact the conductive screw if the neck portions 272.1', 272.2' of the first 272.1 and second 272.2 necked mass elements are either constructed of a non-conductive material or are electrically insulated from the corresponding layer of piezoelectric material 24, 24.1, 24.2. For each layer of piezoelectric material 24.1, 24.2, a corresponding pair of conductive leads 226.1, 226.2 are respectively electrically connected to the corresponding piezoelectric material 24, 24.1, 24.2 and a corresponding side 266.1, 266.2 of the metallic diaphragm disk substrate 266, respectively. The pairs of conductive leads 226.1, 226.2 extend through corresponding through-holes 288 in the sidewall 264 of the hollow housing 256, so as to provide for operatively coupling to, or incorporation in, an associated wiring harness 230, 230', 230" that provides for operatively coupling an electrical signal—responsive to a vibration-induced flexion of the metallic diaphragm disk substrate 266—from the piezoelectric sensor disk 268' to the recording module 32, wherein like-polarity conductive leads 226.1 and 226.2, respectively, are connected in parallel so as to provide for summing the magnitudes of the associated signals from each of the piezoelectric material 24, 24.1, 24.2 in phase with one another.

For yet another example, referring to FIG. 25, a third embodiment 10, $10^{c\prime\prime\prime\prime}$ of the fourth-aspect auscultatory sound-or-vibration sensor 10, $10^{c\prime\prime\prime\prime}$ incorporates a pair of first aspect piezoelectric sensor disks 268.1', 268.2', each of which is similar in construction to that descried hereinabove for the first embodiment 10, $10^{a\prime\prime\prime\prime}$, and similarly amenable to similar alternative configurations. In the third embodiment 10, $10^{c\prime\prime\prime\prime}$ illustrated in FIG. 25, the associated layers of piezoelectric material 24, 24', 24" on the respective first sides 266.1', 266.1" of the corresponding associated metallic diaphragm disk substrates 266, 266', 266" are faced away from one another—with each layer of piezoelectric material 24, 24', 24" located within a different associated cavity 270, 284,—with the corresponding second sides 266.2', 266.2" of the corresponding associated metallic diaphragm disk substrates 266, 266', 266" facing one another, and separated from one another by a pair of concentric spacer rings 290, 292 that engage with the centers and peripheries of the metallic diaphragm disk substrates 266, 266', 266", respectively, and that provide for increased damping of the pair of first aspect piezoelectric sensor disks 268.1', 268.2' relative to that of a single first aspect piezoelectric sensor disks 268.1 alone. The spacer rings 290, 292 may be constructed of the same, above-described materials as used for the hollow housing 256, provided that the associated layers of piezoelectric material 24, 24', 24" does not become electrically shorted to either associated metallic diaphragm disk substrates 266, 266', 266", or each other, thereby. Similar to the second embodiment 10, $10^{b''''}$, for each layer of piezoelectric material 24, 24', 24", a corresponding pair of conductive leads 226.1, 226.2 are respectively electrically connected to the corresponding piezoelectric material 24, 24', 24" and a corresponding side 266.1', 266.1" of the metallic diaphragm disk substrate 266, respectively. The pairs of conductive leads 226.1, 226.2 extend through corresponding through-holes 288 in the sidewall 264 of the hollow housing 256 and through a sidewall of the housing cap 280, so as to provide for operatively coupling to, or incorporation in, an associated wiring harness 230, 230', 230" that provides for operatively coupling an electrical signal—responsive to a vibration-induced flexion of the metallic diaphragm disk substrate 266—from the piezoelectric sensor disk 268' to the recording module 32, wherein like-polarity conductive leads 226.1 and 226.2, respectively, are connected in parallel so as to provide for summing the magnitudes of the associated signals from each of the piezoelectric material 24, 24.1, 24.2 in phase with one another, i.e. with like polarity responsive to the same direction of flexion of the associated metallic diaphragm disk substrate 266, 266'. More particularly, if the layers of piezoelectric material 24, 24', 24" are facing in the same direction, then the conductive leads 226.1 connected to the piezoelectric material 24, 24', 24" would each have the same polarity, as would the conductive leads 226.2 connected to the metallic diaphragm disk substrates 266, 266', 266". If the layers of piezoelectric material 24, 24', 24" are facing in the opposite directions—i.e. either away from one another, or towards one another,—then the conductive leads 226.1 connected to the piezoelectric material 24, 24', 24" would each have the opposite polarity, as would the conductive leads 226.2 connected to the metallic diaphragm disk substrates 266, 266', 266". For example, in accordance with an alternative to the above-described third embodiment 10, $10^{c''''}$, the pair of first aspect piezoelectric sensor disks 268.1', 268.2' could be oriented with the associated layers of piezoelectric material 24, 24', 24" facing one another, and within a third cavity 294 between the metallic diaphragm disk substrates 266, 266', 266" and between the first 270 and second 284 cavities, which would provide for both pairs of conductive leads 226.1 and 226.2 to be routed through a common through-hole 288 in the sidewall 264 of the hollow housing 256.

As best understood, the fourth-aspect auscultatory sound-or-vibration sensor 10, 10"" acts as an accelerometer responsive to the underlying vibrations of the skin 36 of the test subject 34 that are responsive to associated auscultatory sounds or vibrations that are transmitted—via the acoustically-transmissible-adhesive interface 55 operatively coupled to the to the outer surface 258.1 of the flat base 258 of the hollow housing 256—to the hollow housing 256, and thereby to the periphery of the one or more associated piezoelectric sensor disks 268, 268.1', 268.2', 268", which acts to cause a longitudinal vibrational translation thereof in the direction of propagation of the associated ascultatory sounds or vibrations, i.e. substantially normal to the skin 36 of the test subject 34. The translational motion of the hollow housing 256 responsive to the ascultatory sounds or vibrations is impeded by the inertia of the first 272.1 and second 272.2 necked mass elements that collectively act as an inertial mass coupled to center of the associated flexural one or more metallic diaphragm disk substrates 266, 266', 266" to apply a vibratory inertial force to the center(s) of the one or more metallic diaphragm disk substrates 266, 266', 266", resulting in a corresponding associated vibratory flexion thereof and a resulting corresponding associated vibratory electrical signal to be generated by the associated one or more layers of piezoelectric material 24, 24.1, 24.2, 24', 24" responsive thereto, wherein the magnitude of the vibratory inertial force is responsive to the underlying acceleration of the hollow housing 256. The acoustically-transmissible-adhesive interface 55, for example, of a hydrogel material 55, 56, is adapted—where possible, and to the extent possible—to provide for matching the mechanical impedance of the fourth-aspect auscultatory sound-or-vibration sensor 10, 10"" to that of the skin 36 of the test subject 34, so as to increase the transmission of mechanical vibratory power from the skin 36 of the test subject 34 to the hollow housing 256. The fourth-aspect auscultatory sound-or-vibration sensor 10, 10"" is configured to be of relatively-low mass, for example, in the range of 5 to 10 grams for the entire fourth-aspect auscultatory sound-or-vibration sensor 10, 10"", with the combined mass of the hollow housing 256 and associated housing cap 280 prospectively being lower than 2.1 grams for embodiments with a 20 millimeter diameter piezoelectric sensor disk 268, and lower than 4.2 grams for embodiments with a 27 millimeter diameter piezoelectric sensor disk 268, which provides for an associated resonant frequency in the range of 100 to 1,500 Hertz. The relative low mass of the fourth-aspect auscultatory sound-or-vibration sensor 10, 10"" provides for reducing the mechanical loading thereby of the skin 36 of the test subject 34, thereby reducing associated distortion in the measured heart signal. In one set of embodiments, the fourth-aspect auscultatory sound-or-vibration sensor 10, 10"" is adapted to be relatively small,—for example, in one set of embodiments, in the range of 10 to 27 millimeters in diameter, driven by the commercial availability of associated piezoelectric sensor disks 268, 268.1', 268.2', 268"—which, in addition to providing for relatively-low overall mass, provides for flexibility in positioning the fourth-aspect auscultatory sound-or-vibration sensor 10, 10"" on the skin 36 of the test subject 34 and provides the fourth-aspect auscultatory sound-or-vibration sensor 10, 10"" to be held on the skin 36 of the test subject 34 by the acoustically-transmissible-adhesive interface 55 even with the test subject 34 inclined at a relatively steep angle.

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein when used as a logic statement, the expression "A or B" is true if either A or B is true, or if both A and B are true, and when used as a list of elements, the expression "A, B or C" is intended to include all combinations of the elements recited in the expression, for example, any of the elements selected from the group consisting of A, B, C, (A, B), (A, C), (B, C), and (A, B, C); and so on if additional elements are listed. Furthermore, it should also be understood that the indefinite articles "a" or "an", and the corresponding associated definite articles "the' or "said", are each intended to mean one or more unless otherwise stated, implied, or physically impossible. Yet further, it should be understood that the expressions "at least one of A and B, etc.", "at least one of A or B, etc.", "selected from A and B, etc." and "selected from A or B, etc." are each intended to mean either any recited element individually or any combination of two or more elements, for example, any of the elements from the group consisting of "A", "B", and "A AND B together", etc. Yet further, it should be understood that the expressions "one of A and B, etc." and "one of A or B, etc." are each intended to mean any of the recited elements individually alone, for example, either A alone or B alone, etc., but not A AND B together. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of the appended claims, and any and all equivalents thereof.

What is claimed is:

1. A sound-or-vibration sensor, comprising:
   a. a first housing, wherein a first end of said first housing incorporates an open-ended cavity bounded by a base portion and a sidewall, said sidewall is located between said base portion and an opening of said open-ended cavity, a periphery of said opening of an open end of said open-ended cavity abuts an outer rim of said first housing, and said sidewall incorporates a counterbore defining a base rim within said open-ended cavity, wherein said base rim is recessed from said outer rim, and said base rim is proximate to said open end of said open-ended cavity;
   b. a metallic diaphragm disk operatively coupled to said base rim of said first housing, thereby providing for closing said open-ended cavity of said first housing;
   c. a piezoelectric material bonded to said metallic diaphragm disk on a cavity-facing side thereof;
   d. at least one inertial mass either incorporated in, or attached to, said first housing; and
   e. a plastic film adhesively bonded to at least one of said outer rim of said first housing or an outer-facing surface of said metallic diaphragm disk, wherein a cavity-facing surface of said plastic film is at least proximally adjacent to said outer-facing surface of said metallic diaphragm disk, and an outer-facing surface of said plastic film provides for receiving an adhesive acoustic interface material to provide for coupling the sound-or-vibration sensor to a skin surface of a test subject.

2. A sound-or-vibration sensor as recited in claim 1, wherein a periphery of said metallic diaphragm disk is adhesively bonded to said base rim of said first housing.

3. A sound-or-vibration sensor as recited in claim 1, wherein said piezoelectric material is bonded to a relatively-central region of said metallic diaphragm disk.

4. A sound-or-vibration sensor as recited in claim 1, wherein said adhesive acoustic interface material comprises a hydrogel material.

5. A sound-or-vibration sensor as recited in claim 1, wherein said plastic film is exclusively adhesively bonded to said outer rim of said hollow first housing.

6. A sound-or-vibration sensor as recited in claim 1, wherein said plastic film is adhesively bonded to said outer-facing surface of said metallic diaphragm disk.

7. A sound-or-vibration sensor as recited in claim 1, wherein outside surfaces of the sound-or-vibration sensor, excepting an end of said sound-or-vibration sensor incorporating said metallic diaphragm disk and said outer rim of said first housing, are overmolded with an elastomeric material having a durometer in the range of Shore 00-10 to 00-50.

8. A sound-or-vibration sensor as recited in claim 1, wherein at least a portion of said first housing incorporating said outer rim is electrically conductive so as to provide for said outer rim to be in electrical contact with said skin surface of said test subject as an electrode of an associated ECG sensor.

9. A sound-or-vibration sensor as recited in claim 8, wherein said first housing comprises a first portion constructed of an electrically-conductive material and a second portion constructed of an electrically-insulating material, said second portion of said first housing comprises an annular ring located within a sidewall portion of said first portion of said first housing, and said annular ring defines said sidewall bounding said open-ended cavity and incorporates said counterbore defining said base rim.

10. A sound-or-vibration sensor as recited in claim 9, wherein said first housing further comprises a third portion defining said base portion of said open-ended cavity, and said first portion of said first housing is interposed between said second and third portions of said first housing.

11. A sound-or-vibration sensor as recited in claim 8, further comprising a circuit board at a second end of said first housing, wherein said circuit board incorporates a pair of electrical contacts that are electrically connected to said piezoelectric material and to said metallic diaphragm disk, respectively, and said second end of said first housing incorporates a magnetically-permeable material that provides for attracting a magnet of an associated removable connector, wherein said removable connector incorporates a pair of spring-loaded electrical contacts that provide for electrically contacting said pair of electrical contacts of said circuit board.

12. A sound-or-vibration sensor as recited in claim 11, wherein said circuit board incorporates a third electrical contact that is electrically connected to said outer rim, and said removable connector incorporates a third spring-loaded electrical contact that provide for electrically contacting said third electrical contact of said circuit board.

13. A sound-or-vibration sensor as recited in claim 1, further comprising a second housing, wherein said second housing is hollow and incorporates an internal flange and open first and second ends, said base portion of said first housing, inserted in said first end of said second housing, abuts a first side of said internal flange, said at least one inertial mass, inserted in said second end of said second housing, abuts a second side of said internal flange, and said first housing is secured to said at least one inertial mass by a first fastener that clamps said first housing and said at least one inertial mass across said internal flange.

14. A sound-or-vibration sensor as recited in claim 13, further comprising a cover that provides for closing said open second end of said second housing, wherein said cover is secured to said at least one inertial mass by a second fastener.

\* \* \* \* \*